US008415320B2

(12) United States Patent
Whyard et al.

(10) Patent No.: US 8,415,320 B2
(45) Date of Patent: Apr. 9, 2013

(54) DELIVERY OF DSRNA TO ARTHROPODS

(75) Inventors: Steven Whyard, Higgins (AU); Fiona Helen Cameron, Lindfield (AU); Minoo Moghaddam, Pymble (AU); Trevor J. Lockett, Denistone (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 0 days.

(21) Appl. No.: 13/545,604

(22) Filed: Jul. 10, 2012

(65) Prior Publication Data

US 2012/0309813 A1 Dec. 6, 2012

Related U.S. Application Data

(63) Continuation of application No. 13/243,413, filed on Sep. 23, 2011, now Pat. No. 8,263,573, which is a continuation of application No. 10/482,888, filed as application No. PCT/AU02/00897 on Jul. 5, 2002, now Pat. No. 8,101,343.

(30) Foreign Application Priority Data

Jul. 6, 2001 (AU) ....................... PR6215

(51) Int. Cl.
*A61K 48/00* (2006.01)
*C07H 21/02* (2006.01)
*C07H 21/04* (2006.01)

(52) U.S. Cl. .......................... 514/44; 536/23.1; 536/24.5

(58) Field of Classification Search .................. None
See application file for complete search history.

(56) References Cited

U.S. PATENT DOCUMENTS

| | | | |
|---|---|---|---|
| 5,264,221 A | 11/1993 | Tagawa et al. |
| 5,354,854 A | 10/1994 | Bourque et al. |
| 5,413,906 A | 5/1995 | Eberle et al. |
| 5,583,198 A | 12/1996 | Whittaker |
| 5,602,242 A | 2/1997 | Ahlquist et al. |
| 5,665,710 A | 9/1997 | Rahman et al. |
| 5,719,054 A | 2/1998 | Boursnell et al. |
| 5,780,269 A | 7/1998 | Inouye et al. |
| 5,854,224 A | 12/1998 | Lockett et al. |
| 5,869,606 A | 2/1999 | Whittaker |
| 5,906,922 A | 5/1999 | Whittaker et al. |
| 6,135,942 A | 10/2000 | Leptin |
| 6,146,886 A | 11/2000 | Thompson |
| 6,171,612 B1 | 1/2001 | Byk et al. |
| 6,172,048 B1 | 1/2001 | Behr et al. |
| 6,423,885 B1 | 7/2002 | Waterhouse et al. |
| 6,451,603 B1 | 9/2002 | Atkins et al. |
| 6,506,559 B1 | 1/2003 | Fire et al. |
| 6,573,099 B2 | 6/2003 | Graham |
| 6,919,466 B2 | 7/2005 | Lightner et al. |
| 6,933,146 B2 | 8/2005 | Helliwell et al. |
| 7,138,565 B2 | 11/2006 | Waterhouse et al. |
| 7,759,697 B2 | 7/2010 | Graham et al. |
| 8,101,343 B2 | 1/2012 | Whyard et al. |
| 8,168,774 B2 | 5/2012 | Graham et al. |
| 8,183,217 B2 | 5/2012 | Waterhouse et al. |
| 2002/0166144 A1 | 11/2002 | Green et al. |
| 2003/0074684 A1 | 4/2003 | Graham et al. |
| 2003/0079684 A1 | 5/2003 | Graham et al. |
| 2003/0159161 A1 | 8/2003 | Graham et al. |
| 2003/0165894 A1 | 9/2003 | Waterhouse |
| 2004/0064842 A1 | 4/2004 | Graham et al. |
| 2004/0180439 A1 | 9/2004 | Graham et al. |
| 2004/0214330 A1 | 10/2004 | Waterhouse et al. |
| 2004/0237145 A1 | 11/2004 | Graham et al. |
| 2004/0265005 A1 | 12/2004 | Graham et al. |
| 2005/0095199 A1 | 5/2005 | Whyard et al. |
| 2005/0250208 A1 | 11/2005 | Graham et al. |
| 2005/0251877 A1 | 11/2005 | Waterhouse et al. |
| 2006/0014715 A1 | 1/2006 | Graham |
| 2006/0178335 A1 | 8/2006 | Waterhouse et al. |
| 2006/0272049 A1 | 11/2006 | Waterhouse et al. |
| 2007/0056057 A1 | 3/2007 | Waterhouse et al. |
| 2007/0078105 A1 | 4/2007 | Waterhouse et al. |
| 2008/0044906 A1 | 2/2008 | Waterhouse et al. |
| 2008/0104732 A1 | 5/2008 | Waterhouse et al. |
| 2011/0076681 A1 | 3/2011 | Waterhouse et al. |
| 2012/0041053 A1 | 2/2012 | Whyard et al. |

FOREIGN PATENT DOCUMENTS

| | | |
|---|---|---|
| EP | 0387775 | 9/1990 |
| EP | 0532380 | 3/1993 |
| EP | 0779365 A2 | 6/1997 |
| EP | 0784094 A1 | 7/1997 |
| WO | WO 94/03607 | 2/1994 |

(Continued)

OTHER PUBLICATIONS

U.S. Appl. No. 09/056,767, filed Apr. 8, 1998 (Peter Michael Waterhouse et al.).
U.S. Appl. No. 09/100,813, filed Jun. 19, 1998 (Michael Wayne Graham).
U.S. Appl. No. 09/127,735, filed Aug. 3, 1998 (Peter Michael Waterhouse et al.).
U.S. Appl. No. 09/287,632, filed Apr. 7, 1999 (Peter Michael Waterhouse et al.).
May 16, 2011 Request for Revocation Under s72 UK Patent Act 1977 of G82353282.
Nov. 2, 2010 Communication from the UK Intellectual Property Office in connection with GB 2353282, including a Request for Revocation Under s72 UK Patent Act 1977 filed Sep. 29, 2010 and amended Request for Revocation Under s72 UK Patent Act 1977 filed Oct. 28, 2010.

(Continued)

*Primary Examiner* — Amy Bowman
(74) *Attorney, Agent, or Firm* — John P. White; Gary J. Gershik; Cooper & Dunham LLP

(57) ABSTRACT

The invention is to methods of gene silencing in arthropods using dsRNA. The method is include contacting the arthropod with, and/or directly feeding the arthropod, the dsRNA to the arthropods to deliver the dsRNA to arthropod tissues. It is envisaged that the methods of the invention will have use in determining the biological function of genes in arthropods. Methods of pest control of arthropods, and of protecting arthropods against parasites and predators are provided. Transgenic arthropods expressing dsRNA molecules are also provided by the present invention.

20 Claims, 6 Drawing Sheets

FOREIGN PATENT DOCUMENTS

| WO | WO94/07367 | 4/1994 |
|---|---|---|
| WO | WO95/08350 | 3/1995 |
| WO | WO 96/05218 | 2/1996 |
| WO | WO 96/40062 | 12/1996 |
| WO | WO 97/04787 | 2/1997 |
| WO | WO 97/49814 | 12/1997 |
| WO | WO 98/50408 A1 | 11/1998 |
| WO | WO 99/32619 | 7/1999 |
| WO | WO 99/49029 | 9/1999 |
| WO | WO 99/53050 | 10/1999 |
| WO | WO 00/32779 | 6/2000 |
| WO | WO 00/55178 A1 | 9/2000 |
| WO | WO 00/55376 A1 | 10/2000 |
| WO | WO 00/63397 | 12/2000 |
| WO | WO 00/76308 | 12/2000 |
| WO | WO 01/19857 A2 | 5/2001 |
| WO | WO 01/34815 A1 | 5/2001 |
| WO | WO 01/38359 A2 | 5/2001 |
| WO | WO 01/37654 A2 | 7/2001 |
| WO | WO 01/49844 | 7/2001 |
| WO | WO 03004644 A1 | 1/2003 |
| WO | WO 03/095647 A2 | 11/2003 |

OTHER PUBLICATIONS

Counter-Statement of Commonwealth Scientific and Industrial Research Organisation in connection with Application Under s72 UK Patent Act 1977 to Revoke Patent No. GB 2353282.
Examination Report issued Mar. 4, 2011 in connection with European Application No. 04015041.9.
Examination Report issued Mar. 4, 2011 in connection with European Application No. 05013010.3.
Examination Report issued May 10, 2010 in connection with European Patent Application No. 02748428.6, issued by the European Patent Office.
Examination Report, issued Aug. 18, 2006, in connection with European Patent Application No. 02 748 428.6-2403, issued by the European Patent Office.
Reply to Notice of Loss of Rights Pursuant to Rule 112(1) EPC submitted Apr. 3, 2009 in connection with European Patent Application No. 04 818 796.7-1212, filed on Nov. 17, 2004.
Examination Report, issued Aug. 22, 2006, in connection with Australian Patent Application No. 2002318971, issued by IP Australia of the Australian Government.
Examination Report, issued Aug. 3, 2004, in connection with New Zealand Patent Application No. 530969, issued by Intellectual Property Office of New Zealand.
Examination Report, issued Dec. 21, 2006, in connection with Australian Patent Application No. 2002318971, issued by IP Australia of the Australian Goverment.
Examination Report, issued Jan. 6, 2009, in connection with Japanese Patent Application No. 2003-510802, issued by the Japan Patent Office.
Examination Report, issued Mar. 11, 2004, in connection with New Zealand Patent Application No. 530969, issued by Intellectual Property Office of New Zealand.
Examination Report, issued May 12, 2009, in connection with Japanese Patent Application No. 2009-091663, issued by the Japan Patent Office.
Examination Report, issued May 20, 2008, in connection with Japanese Patent Application No. 2003-510802, issued by the Japan Patent Office.
Office Action issued Dec. 16, 2010 in connection with Canadian Patent Application No. 2,455,490.
Office Action issued Aug. 28, 2009 in connection with Canadian Patent Application No. 2455490, issued by the Canadian Intellectual Property Office.
Extended European Search Report issued Mar. 14, 2011 in connection with European Patent Application No. 10184533.7.
Supplementary European Search Report issued Feb. 12, 2010 in connection with European Patent Application No. 04761272.
Supplementary Partial European Search Report, EP Application No. 02748428.6, dated Feb. 17, 2006, 7 pages.
Feb. 17, 2006 Communication and Supplementary European Search Report for EP Application No. EP 02 748428.
Final Rejection issued Nov. 2, 2010 in connection with Japanese Patent Application No. 2009-091663 (with English Translation).
International Preliminary Examination Report for PCT International Application No. PCT/AU02/00897 dated Oct. 10, 2003, 5 pages.
International Search Report for PCT International Application No. PCT/AU02/00897 dated Aug. 12, 2002, 6 pages.
Allen et al. (2007) "Development of strategies for conditional RNA interference," J. Gene Med. 9: 287-298.
Allen, T. M. et al., Large unilamellar liposomes with low uptake the reticuloendothelial system, FEBS Lett. 223(1):42-46, 1987.
Appel, H. M. and L. W. Maines. The influence of host plant on gut conditions on gypsy moth (Lymantria dispar) caterpillars. J. Insect Phys 1995. 41:241-246.
Baulcomb (1996), "Mechanisms of Pathogen-Derived Resistance to Viruses in Transgenic Plants," Plant Cell, vol. 8:1833-1844.
Beck, J., et al. (1995), "Efficient hammerhead ribozyme-mediated cleavage of the structured hepatitis B virus encapsidation signal in vitro and in cell extracts, but not in intact cells," Nucleic Acids Research, vol. 23, No. 24: 4954-4962.
Bloomfield, DNA Condensation by Multivalent Cation, Biopolymers: Nucleic Acid Science, 1997.
Bosher, J. M. et al., "RNA interference: genetic wand and genetic watchdog," Nature Cell Biol. 2:E31-E36, 2000.
Bourque et al. (1992), "Suppression of gene expression in plant cells utilizing antisense sequences transcribed by RNA polymerase III," Plant Molecular Biology 19:641-647.
Brown et al. (1999) "Using RNAi to investigate orthologous homeotic gene function during development of distantly related insects," Evolution and Development, vol. 1. issue 1, pp. 11-15.
Cameron, F. H. et al., uA transfection compound series based on a versatile Tris linkage, Biochim. Biophys. Acta 1417:37-50, 1999.
Cameron et al. (1999), "A transfection compound series based on a versatile Tris linkage," Biochim. Biophys. Acta, 7(1), pp. 37-50.
Caplen, N. J. et al., dsRNA-mediated gene silencing in cultured *Drosophila* cells: a tissue culture model for the analysis of RNA interference: Gene 252:95-100,2000.
Caplen, N. J. et al., "dsRNA-mediated gene Silencing in cultured *Drosophila* cells: A tissue culture model for the analysis of RNA interference," Gene 252(1-2):95-105, 2000.
Carthew, R. W., "Gene Silencing by double-stranded RNA," Curro Opin. Cell Biol. 13(2):244-248, 2001.
Davenloo, P. et al. (1984) "Cloning and expression of the gene for bacteriophage T7 RNA polymerase," PNAS vol. 81, pp. 2035-2039.
De Angelis, F.G., et al. (2002), "Chimeric snRNA molecules carrying antisense sequences against the splice junctions of exon 51 of the dystrophin pre-mRNA induce exon skipping and restoration of a dystrophin synthesis in delta 48-50 DMD cells," PNAS, vol. 99, No. 14: 9456-9461.
Declaration of David M. Stalker filed in opposition to Australian Patent Application No. 778474 (Nov. 4, 2008).
Doelling et al. (1995), PNAS vol. 8:683-692.
Dougherty, W. G. et al., "Transgenes and gene suppression: telling us something new?" Curro Opin. Cell Biol. 7:399-405, 1995.
Duve, H. et al., Lepidopteran peptides of the allatostatin superfamily, Peptides 18 (9) :1301-1309, 1997.
Ecker, J.R., Davis, R.W., (1986) "Inhibition of gene expression plant cells by expression of antisense RNA," PNAS 83(15): 5372-5376.
Elbashir, S. M. et aI., "Duplexes of 21-nucleotide RNAs mediate RNA interference in cultured mammalian cells," Nature 411 :494-498, 2001.
Furusawa, T., Takayama E., Ishihara, R. and Hayashi, Y. Double-stranded Ribonuclease Activity in the Digestive Juice and Midgut of the Silkworm, *Bombyx Mori*. Comp. Biochem. Physiol. 1993; 104B(4) :795-801.
Gao and Huang, "Cationic liposome-mediated gene transfer", Gene Therapy (1995), 2:710-722.
Gatz, C. (1997), "Chemical Control of Gene Expression," Annu. Rev. Plant Physiol. Plant Mol. Bio. 48:89-108.

Gawron-Burke, C. et al., "Genetic manipulation of ba~illus thuringiensis insecticidal crystal protein genes in bacteria," In: Genetic Engineering: Principles and Methods, vol. 13. J. K. Setlow (ed.), Plenum Press, New York, pp. 237-263, 1991.
Genbank Accession No. A65102, Nov. 14, 2006.
Genbank Accession No. AF 124360, Jul. 21, 2000.
Genbank Accession No. AF043841, Jun. 5, 1999.
Genbank Accession No. L26296, Jun. 28, 1994.
Goto, A. et al., *Drosophila* mitochondrial transcription factor A (d-TFAM) is dispensable for the transcription of AB mitochondrial DNA in Kc167 cells: Biochem J 354:243-248, 2001.
Goto, A. et al., "*Drosophila* mitochondrial transcription factor A (d-TFAM) is dispensable for the transcription of mitochondrial DNA in Kc167 cells," Biochem. J. 354:243-248, 2001.
Gura T. A silence that speaks volumes. Nature. Apr. 20, 2000; 404(6780) : 804-8.
Guy-Caffrey et al., "Novel Polyaminolipids Enhance the Cellular Update of Oligonucleotides (1995)," JBC, vol. 270, No. 52, pp. 31391-31396.
Image of U6 snoRNA secondary structure retrieved from http://gene.fudan.sh.cn/snoRNASecStruct/Box&20C&D/Homo&20sapiens/U16_ssp0001.jpg on Sep. 17, 2009.
Izant and Weintraub (1984) "Inhibition of Thymidine Kinase Gene Expression by Anti-Sense RNA: A molecular Approach to Genetic Analysis," Cell vol. 36, 1007-1015.
Kennerdell, J. R. et al. , "Heritable gene Silencing in *Drosophila* using doublestranded RNA," Nature Biotechnology 18:896-898, 2000.
Kennerdel et al. (1998), "Use of dsRNA-Mediated Genetic Interference to Demonstrate that frizzled and frizzled 2 Act in the Wingless Pathway," Cell, vol. 95, pp. 1017-1026.
Maeda, I. et al., "Large-scale analysis of gene function in Caenornabditis elegans by high-throughput NRAI, "Current Biology 11:171-176, 2001.
Marshallsay et al. (1992) "Characterization of the U3 and U6 snRNA genes from wheat: U3 snRNA genes in monocot plants are transcribed by RNA polymerase III," Plant Molecular Biology, vol. 19, pp. 973-983.
Martinek, S. and Young, M.W., "Specific genetic interference with behavioral rhythms in *Drosophila* by expression of inverted repeats", Genetics (2000), 156:1717-1725.
Methods in Enzymology, vol. 185: Gene Expression Technology, edited by David V. Goeddel (1992).
Miller SC, Brown SJ, Tomoyasu Y. Larval RNAi in *Drosophila*? Dev Genes Evol. Sep. 2008;218(9):505-10.
Mishra et al. (1998), "Post-transcriptional silencing of pectin methylesterase gene in transgenic tomato fruits results from impaired pre-mRNA processing," The Plant Journal 14(5): 583-592.
Misquitta, I. et al., "Targeted disruption of gene function in *Drosophila* by RNA interference (RNA-i): A role for nautilus in embryonic somatic muscle formation," Proc. Natl. Acad. Sci. USA 96(4):1451-1456, 1999.
Murfett et al. (1995), "Antisense suppression of S-Rnase expression in Nicotiana using RNA polymerase II- and III-transcribed gene constructs," Plant Molecular Biology 29:21-212.
Needleman, S. B. at al., "A general method applicable to the search for similarities in the amino acid sequence of two proteins," J. Mol. Biol. 48:443-453, 1970.
Nobelprize.org: The Nobel Prize in Physiology or Medicine 2006, Press Release of the Nobel Assembly at Karolinska Institute (Oct. 2, 2006).
Patankar AG, Giri AP, Harsulkar AM, Sainani MN, Deshpande VV, Ranjekar PK, Gupta VS.Complexity in specificities and expression of Helicoverpa armigera gut proteinases explains polyphagous nature of the insect pest. Insect Biochem Mol Biol. Mar. 15, 2001;31 (4-5):453-64.
Piccin, A. et al., "Efficient and heritable functional knock-out of an adult phenotype in *Drosophila* using a GAL4-driven hairpin RNA incorporating a heterologous spacer," Nucleic Acids Research 29(12):e55/1-e55/5, 2001.
Rajagopal R, Sivakumar S, Agrawal N, Malhotra P, Bhatnagar RK. Silencing of midgut aminopeptidase N of Spodoptera litura by double-stranded RNA establishes its role as Bacillus thuringiensis toxin receptor. J Biol Chem. Dec. 6, 2002;277(49):46849-51.
Rosenberg, A. et al. (1987) "Vectors for selective expression of cloned DNAs by T7 RNA polymerase," Gene. 1987;56(1):125-35.
Scholthof et al. (1996), "Plant Virus Gene Vectors for Transient of Expression Foreign Proteins in Plants," Annu. Rev. of Phytopathol. 34:299-323.
Shimizu et al. (1997) Biol. Pharm. Bull. 20(8), pp. 881-886.
Spradling, A. C. et al., "Transposition of cloned P elements into *Drosophila* germ line chromosomes," Science 218:341-347 1982.
Steinbrecher, R. (2002), "The CamV 35S Promoter, Government and Corporate Scientific Incompetence: Failure to assess the safety of GM crops," EcoNexus Briefing Dec. 2002.
Suter, D., et al. (1999), "Double-target antisense U7 snRNAs promote efficient skipping of an aberrant exon in three human beta-thalassemic mutations," Human Molecular Genetics, vol. 8: 2415-2423.
Tabara, H. et al.. "RNAi C. elegans: soaking in the genome sequence," Science 282:430-431, 1998.
Tatsuo, et al. (1997) "Comparison of three non-viral transfection methods for foreign gene expression in early chicken embryos in ovo," Biochemical and Biophysical Research Communications 230, 376-380.
Terra, W. R., C. Ferreira, and J. E. Baker, Compartmentalization digestion. Ed. M. J. Lehane and P. F. Billingsley. Biology of the insect midgut 1996. 206-235. Chapman & Hall London.
Thummel, C. S. et al., "Vectors for *Drosophila* P-element-mediated and transformation tissue culture transfection"Gene 74:445-456 1988.
Tieman et al. (1992), "An Antisense Pectin Methylesterase Gene Alters Pectin Chemistry and Soluble Solids in Tomato Fruit," The Plant Cell, vol. 4:667-679.
Timmons, L. et al., "Specific interference by ingested dsRNA," Nature 395:354, 1998.
Vance, V. et al., "RNA silencing in plants—defense and counterdefense," Science 292:2277-2280 2001.
Waibel et al. (1990) "RNA polymerase specificity of transcription of Arabidopsis U snRNA genes determined by promoter element spacing," Letters to Nature, vol 346, pp. 199-202).
Waibel et al., (1990) "U6 snRNA genes of Arabidopsis are transcribed by RNA polymerase III but contain the same two upstream promoter elements as RNA polymerase II transcribed U-snRNA genes," Nucleic Acids Research, vol. 18, No. 12, pp. 3451-3458.
Waterhouse, P. M. et al., "Virus resistance and gene silencing in plants can be induced by simultaneous expression of sense and antisense RNA," Proc. Natl. Acad. Sci. 95:13959-13964 1998.
Waterhouse, P. M. et al., "Gene silencing as an adaptive defence against viruses," Nature 411:834-842, 2001.
Weiher and Komnick (Archives of Insect Biochemistry and Physiology 36:273-293 (1997).
Wharton et al. (1994) Journal of General Virology, 75:945-948.
Wolff et al. (1995) "Mutational analysis of human U6 RNA: stabilizing the intramolecular helix blocks the spliceosomal assembly pathway," Biochim. Biophys. Acta 1263: 39-44.
Wu, N. Z. et al., "Increased microvascular permeability contributes to preferential accumulation of stealth liposomes in tumor tissue," Cancer Research 53:3765-3770, 1993.
Yang, D. et al., "Evidence that processed small dsRNAs may mediate sequence-specific mRNA degradation during RNAi in *Drosophila* embryos", Research Paper Current Biology (2000), 10:1191-1200.
Zamore, P.D., "RNA interference: Listening to the sound of silence," Nat. Struct. Biol. 8(9):746-750, 2001.
Zamore, P.D., et al. (2000) "RNAi: Double-Stranded RNA Directs the ATP-Dependent Cleavage of mRNA at 21 to 23 Nucleotide Intervals," *Cell* 101:25-33.
File of Re-examination Control No. 90/008,096, filed May 18, 2006 including all references cited and disclosed, rejections and arguments therein (reexamination of U.S. Patent No. 6,573,099, issued Jun. 3, 2003 from U.S. Appl. No. 09/100,812).
File of Re-examination Control No. 90/007,247, filed Oct. 4, 2004 including all references cited and disclosed, rejections and arguments therein (reexamination of U.S. Patent No. 6,573,099, issued Jun. 3, 2003 from U.S. Appl. No. 09/100,812).

Request for Re-examination Pursuant to 35 U.S.C. §§ 302-307 and 37 C.F.R. § 1.510, submitted Oct. 4, 2004 in connection with U.S. Reexamination No. 90/007,247, filed Oct. 4, 2004.
Order Granting / Denying Request for Ex Parte Reexamination issued Dec. 7, 2004 in connection with U.S. Reexamination No. 90/007,247, filed Oct. 4, 2004.
U.S. re-examination No. 90/007,247, filed Oct. 4, 2004, of U.S. Patent No. 6,573,099, including documents of record therein.
Office Action issued Aug. 31, 2005 in connection with U.S. Reexamination No. 90/007,247, filed Oct. 4, 2004.
Ex Parte Reexamination Interview Summary issued Oct. 25, 2005 in connection with U.S. Reexamination No. 90/007,247, filed Oct. 4, 2004.
Amendment submitted Nov. 28, 2005 in connection with U.S. Reexamination No. 90/007,247, filed Oct. 4, 2004.
Statement of the Content of the Interview Under 37 C.F.R. § 1.560(b) included with the Amendment submitted Nov. 28, 2005 in connection with U.S. Reexamination No. 90/007,247, filed Oct. 4, 2004.
Declaration of Michael Graham Under 37 C.F.R. § 1.132 included with the Amendment submitted Nov. 28, 2005 in connection with U.S. Reexamination No. 90/007,247, filed Oct. 4, 2004.
Letter to Examiner submitted Mar. 1, 2006, including a communication from the Australian Patent Office in connection with U.S. Reexamination No. 90/007,247, filed Oct. 4, 2004.
Office Action issued Apr. 12, 2006 in connection with U.S. Reexamination No. 90/007,247, filed Oct. 4, 2004.
Notice of Failure to Comply with *Ex Parte* Reexamination Request Filing [37 CFR 1.510(c)] issued May 23, 2006 in connection with U.S. Reexamination No. 90/008,096, filed May 18, 2006.
Amendment submitted Jun. 12, 2006 in connection with U.S. Reexamination No. 90/007,247, filed Oct. 4, 2004.
Declaration [of Michael Graham, Ph.D.] Under 37 C.F.R. § 1.131 included the Amendment submitted Jun. 12, 2006 in connection with U.S. Reexamination No. 90/007,247, filed Oct. 4, 2004.
Request for Reexamination Pursuant to 35 U.S.C. §§ 302-307 and 37 C.F.R. §§1.502 and 1.510, submitted May 18, 2006 in connection with U.S. Reexamination No. 90/008,096, filed May 18, 2006.
Reply to Notice of Failure to Comply with *Ex Parte* Reexamination Request Filing Reguirements submitted Jun. 14, 2006 in connection with U.S. Reexamination No. 90/008,096, filed May 18, 2006.
Order Granting / Denying Request for Ex Parte Reexamination issued Jul. 20, 2006 in connection with U.S. Reexamination No. 90/008,096, filed May 18, 2006.
Housekeeping Amendment submitted Nov. 27, 2006 in connection with U.S. Reexamination No. 90/008,096, filed May 18, 2006.
Office Action issued Jan. 24, 2007 in connection with Merged Reexamination Nos. 90/007,247 and 90/008,096, filed Oct. 4, 2004 and May 18, 2006, respectively.
Summary of the Substance of the Interview and Comments on Examiner's Notes submitted Mar. 16, 2007 in connection with Merged Reexamination Nos. 90/007,247 and 90/008,096, filed Oct. 4, 2004 and May 18, 2006, respectively.
Interview Summary issued Mar. 2, 2007 in connection with Merged Reexamination Nos. 90/007,247 and 90/008,096, filed Oct. 4, 2004 and May 18, 2006, respectively.
Amendment submitted Apr. 24, 2007 in connection with Merged Reexamination Nos. 90/007,247 and 90/008,096, filed Oct. 4, 2004 and May 18, 2006, respectively.
Declaration [of Michael Graham, Ph.D.] Under 37 C.F.R. § 1.131 included with the Amendment submitted Apr. 24, 2007 in connection with Merged Reexamination Nos. 90/007,247 and 90/008,096, filed Oct. 4, 2004 and May 18, 2006, respectively.
Declaration [of Kenneth Reed, Ph.D.] Under 37 C.F.R. § 1.131 included with the Amendment submitted Apr. 24, 2007 in connection with Merged Reexamination Nos. 90/007,247 and 90/008,096, filed Oct. 4, 2004 and May 18, 2006, respectively.
Interview Summary issued Jul. 6, 2007 in connection with Merged Reexamination Nos. 90/007,247 and 90/008,096, filed Oct. 4, 2004 and May 18, 2006, respectively.
Amendment submitted Aug. 3, 2007 in connection with Merged Reexamination Nos. 90/007,247 and 90/008,096, filed Oct. 4, 2004 and May 18, 2006, respectively.

Statement of the Content of the Interview Under 37 C.F.R. § 1.5600(b) included with the Amendment submitted Aug. 3, 2007 in connection with Merged Reexamination Nos. 90/007,247 and 90/008,096, filed Oct. 4, 2004 and May 18, 2006, respectively.
Amendment submitted Nov. 28, 2007 in connection with Merged Reexamination Nos. 90/007,247 and 90/038,096, filed Oct. 4, 2004 and May 18, 2006, respectively.
Mar. 7, 2008 Communication to the Examiner, including Mar. 7, 2008 Declaration of Michael Graham Ph.D., in connection with Merged Reexamination Nos. 90/007,247 and 90/008,096, filed Oct. 4, 2004 and May 18, 2006, respectively.
Office Action issued Apr. 11, 2008 in connection with Merged Reexamination Nos. 90/007,247 and 90/008,096, filed Oct. 4, 2004 and May 18, 2006, respectively.
Interview Summary issued Jun. 12, 2008 in connection with Merged Reexamination Nos. 90/007,247 and 90/008,096, filed Oct. 4, 2004 and May 18, 2006, respectively.
Amendment submitted Jul. 11, 2008 in connection with Merged Reexamination Nos. 90/007,247 and 90/008,096, filed Oct. 4, 2004 and May 18, 2006, respectively.
Office Action issued Nov. 19, 2008 in connection with Merged Reexamination Nos. 90/007,247 and 90/008,096, filed Oct. 4, 2004 and May 18, 2006, respectively.
Office Action issued Nov. 26, 2008 in connection with Merged Reexamination Nos. 90/007,247 and 90/008,096, filed Oct. 4, 2004 and May 18, 2006, respectively.
Interview Summary issued Feb. 12, 2009 in connection with Merged Reexamination Nos. 90/007,247 and 90/008,096, filed Oct. 4, 2004 and May 18, 2006, respectively.
Amendment after Final submitted Feb. 26, 2009 in connection with Merged Reexamination Nos. 90/007,247 and 90/008,096, filed Oct. 4, 2004 and May 18, 2006, respectively.
Declaration of Dr. Arthur Riggs Under Under 37 C.F.R. §1.132, including Exhibits A to I submitted Feb. 26, 2009 in connection with Merged Reexamination Nos. 90/007,247 and 90/008,096, filed Oct. 4, 2004 and May 18, 2006, respectively.
Advisory Action issued Mar. 25, 2009 in connection with Merged Reexamination Nos. 90/007,247 and 90/008,096, filed Oct. 4, 2004 and May 18, 2006, respectively.
Petition Under 37 C.F.R. § 1.181 submitted Apr. 3, 2009 in with connection with Merged Reexamination Nos. 90/007,247 and 90/008,096, filed Oct. 4, 2004 and May 18, 2006, respectively.
Petition for Extension of Time submitted Apr. 22, 2009 in connection with Merged Reexamination Nos. 90/007,247 and 90/008,096, filed Oct. 4, 2004 and May 18, 2006, respectively.
Advisory Action issued Apr. 24, 2009 in connection with Merged Reexamination Nos. 90/007,247 and 90/008,096, filed Oct. 4, 2004 and May 18, 2006, respectively.
Decision on Petition Under 37 C.F.R. § 1.181 issued Apr. 25, 2009 in connection with Merged Reexamination Nos. 90/007,247 and 90/008,096, filed Oct. 4, 2004 and May 18, 2006, respectively.
Decision on Petition for Extension of Time issued Apr. 27, 2009 in connection with Merged Reexamination Nos. 90/007,247 and 90/008,096, filed Oct. 4, 2004 and May 18, 2006, respectively.
Appeal Brief submitted Jul. 27, 2009 in connection with Merged Reexamination Nos. 90/007,247 and 90/008,096, filed Oct. 4, 2004 and May 18, 2006, respectively.
Notification of Non-compliant Appeal Brief in Ex Parte Reexamination issued Oct. 22, 2009 in connection with Merged Reexamination Nos. 90/007,247 and 90/008,096, filed Oct. 4, 2004 and May 18, 2006, respectively.
Communication in Response to Notification of Non-compliant Appeal Brief submitted Nov. 2, 2009 in connection with Merged Reexamination Nos. 90/007,247 and 90/008,096, filed Oct. 4, 2004 and May 18, 2006, respectively.
Examiner's Answer issued Jan. 7, 2010 in response to applicant's Appeal Brief filed Jul. 27, 2009 in connection with Merged Reexamination Nos. 90/007,247 and 90/008,096, filed Oct. 4, 2004 and May 18, 2006, respectively.
Reply Brief to Examiner's Answer submitted on Mar. 8, 2010, in connection with merged Reexamination Control Nos. 90/007,247 and 90/008,096, filed Oct. 4, 2004 and May 18, 2006, respectively.

Request for Oral Rearing submitted Mar. 8, 2010, in connection with merged Reexamination Control Nos. 90/007,247 and 90/008,096, filed Oct. 4, 2004 and May 18, 2006, respectively.
Sep. 29, 2010 Decision of the BPAI in connection with merged Reexamination Control Nos. 90/007,247 and 90/008,096, filed Oct. 4, 2004 and May 18, 2006, respectively.
Nov. 5, 2010 Notice of Intent to Issue Reexamination Certificate in connection with merged Reexamination Control Nos. 90/007,247 and 90/008,096, filed Oct. 4, 2004 and May 18, 2006, respectively.
Ex parte Reexamination Certificate issued Mar. 8, 2011 in connection with merged Reexamination Control Nos. 90/007,247 and 90/008,096, filed Oct. 4, 2004 and May 18, 2006, respectively.
Complete file history for U.S. Published Application No. 2004/0266005 A1, published Dec. 30, 2004 (U.S. Appl. No. 10/821,726, filed Apr. 8, 2004; Michael Wayne Graham et al.).
Preliminary Amendment submitted Apr. 8, 2004 in connection with U.S. Appl. No. 10/821,726, filed Apr. 8, 2004.
Petition to Make Special Under 37 CFR 1.102(d) submitted Jul. 28, 2004 in connection with U.S. Appl. No. 10/821,726, filed Apr. 8, 2004.
Decision on Petition to Make Special Under 37 CFR 1.102(d) issued Jul. 28, 2004 in connection with U.S. Appl. No. 10/821,726, filed Apr. 8, 2004.
Office Action issued Oct. 14, 2005 in connection with U.S. Appl. No. 10/821,726, filed Apr. 8, 2004.
Amendment submitted Nov. 14, 2005 in connection with U.S. Appl. No. 10/821,726, filed Apr. 8, 2004.
Office Action issued May 30, 2006 in connection with U.S. Appl. No. 10/821,726, filed Apr. 8, 2004.
Amendment submitted Nov. 30, 2006 in connection with U.S. Appl. No. 10/821,726, filed Apr. 8, 2004.
Amendment submitted Dec. 14, 2006 in connection with U.S. Appl. No. 10/821,726, filed Apr. 8, 2004.
Communication issued Apr. 2, 2007 in connection with U.S. Appl. No. 10/921,726, filed Apr. 8, 2004.
Amendment submitted Aug. 2, 2007 in connection with U.S. Appl. No. 10/821,726, filed Apr. 8, 2004.
Amendment submitted Oct. 31, 2007 in connection with U.S. Appl. No. 10/821,726, filed Apr. 8, 2004.
Office Action issued Nov. 6, 2007 in connection with U.S. Appl. No. 10/821,726, filed Apr. 8, 2004.
Request to Correct Inventorship Under 37 C.F.R. §1.48(a) submitted Dec. 12, 2007 in connection with U.S. Appl. No. 10/821,726, filed Apr. 8, 2004.
Office Action issued Sep. 2, 2008 in connection with U.S. Appl. No. 10/821,726, filed Apr. 8, 2004.
Amendment, including Exhibits A to C submitted Sep. 5, 2008 in connection with U.S. Appl. No. 10/821,726, filed Apr. 8, 2004.
Amendment and Request for Continued Examination Submitted Sep. 5, 2008 in connection with U.S. Appl. No. 10/821,726, filed Apr. 8, 2004.
Office Action issued Nov. 3, 2008 in connection with U.S. Appl. No. 10/821,726, filed Apr. 8, 2004.
Amendment submitted May 4, 2009 in connection with U.S. Appl. No. 10/821,726, filed Apr. 8, 2004.
Supplemental Amendment to May 4, 2009 Amendment Filed in Response to Nov. 3, 2008 Office Action and Supplemental Information Disclosure Statement submitted Oct. 7, 2009 in connection with U.S. Appl. No. 10/821,726, filed Apr. 8, 2004.
Notice to the applicant regarding a non-compliant or non-responsive amendment issued Sep. 4, 2009 in connection with U.S. Appl. No. 10/821,726, filed Apr. 8, 2004.
Communication in response to a non-compliant or non-responsive amendment submitted Oct. 5, 2009 in connection with U.S. Appl. No. 10/821,725, filed Apr. 8, 2004.
Office Action issued Mar. 9, 2010 in connection with U.S. Appl. No. 10/821,726, filed Apr. 8, 2004.
Amendment and Supplemental Information Disclosure Statement as a Submission Accompanying a Request for Continued Examination filed Dec. 15, 2010 in connection with U.S. Appl. No. 10/821,726, filed Apr. 8, 2004.
Supplemental Information Disclosure Statement filed Jun. 22, 2011 in connection with U.S. Appl. No. 10/821,726, filed Apr. 8, 2004.

Office Action issued Mar. 22, 2011 in connection with U.S. Appl. No. 10/321,726, filed Apr. 8, 2004.
Amendment and Supplemental Information Disclosure Statement filed Jun. 22, 2011 in connection with U.S. Appl. No. 10/821,726, filed Apr. 8, 2004.
Jul. 25, 2011 Notice of Allowance issued in connection with U.S. Appl. No. 10/821,726, filed Apr. 8, 2004.
Communication issued Jun. 2, 1999 in connection with U.S. Appl. No. 09/287,632, filed Apr. 7, 1999.
Preliminary Amendment submitted Jun. 28, 1999 in connection with U.S. Appl. No. 09/287,632, filed Apr. 7, 1999.
Office Action issued Oct. 3, 2000 in connection with U.S. Appl. No. 09/287,632, filed Apr. 7, 1999.
Communication issued Jul. 21, 2000 in connection with U.S. Appl. No. 09/287,632, filed Apr. 7, 1999.
Amendment submitted Aug. 21, 2000 in connection with U.S. Appl. No. 09/287,632, filed Apr. 7, 1999.
Amendment submitted Mar. 5, 2001 in connection with U.S. Appl. No. 09/287,632, filed Apr. 7, 1999.
Communication submitted May 18, 2001 in connection with U.S. Appl. No. 09/287,632, filed Apr. 7, 1999.
Amendment submitted Jun. 11, 2001 in connection with U.S. Appl. No. 09/287,632, filed Apr. 7, 1999.
Communication issued Aug. 21, 2001 in connection with U.S. Appl. No. 09/287,632, filed Apr. 7, 1999.
Amendment submitted Aug. 24, 2001 in connection with U.S. Appl. No. 09/287,632, filed Apr. 7, 1999.
Office Action issued Nov. 2, 2001 in connection with U.S. Appl. No. 09/287,632, filed Apr. 7, 1999.
Amendment submitted Apr. 2, 2002 in connection with U.S. Appl. No. 09/287,632, filed Apr. 7, 1999.
Advisory Action issued Apr. 11, 2002 in connection with U.S. Appl. No. 09/287,632, filed Apr. 7, 1999.
Office Action issued Jul. 16, 2002 in connection with U.S. Appl. No. 09/287,632, filed Apr. 7, 1999.
Interview Summary of Sep. 5, 2002 Interview in connection with U.S. Appl. No. 09/287,632, filed Apr. 7, 1999.
Amendment submitted Jan. 16, 2003 in connection with U.S. Appl. No. 09/287,632, filed Apr. 7, 1999.
Office Action issued Apr. 9, 2003 in connection with U.S. Appl. No. 09/287,632, filed Apr. 7, 1999.
Amendment submitted Jul. 7, 2003 in connection with U.S. Appl. No. 09/287,632, filed Apr. 7, 1999.
Communication issued Mar. 25, 2004 in connection with U.S. Appl. No. 09/287,632, filed Apr. 7, 1999.
Interview Summary issued Jul. 29, 2004 in connection with U.S. Appl. No. 09/287,632, filed Apr. 7, 1999.
Summary of Interview submitted Aug. 6, 2004 in connection with U.S. Appl. No. 09/287,632, filed Apr. 7, 1999.
Office Action issued Nov. 3, 2004 in connection with U.S. Appl. No. 09/287,632, filed Apr. 7, 1999.
Communication issued Dec. 3, 2004, in connection with U.S. Appl. No. 09/287,632, filed Apr. 7, 1999.
Office Action issued Mar. 11, 2005 in connection with U.S. Appl. No. 09/287,632, filed Apr. 7, 1999.
Amendment submitted Sep. 12, 2005, in connection with U.S Appl. No. 09/287,632, filed Apr. 7, 1999.
Office Action issued Nov. 10, 2005 in connection with U.S. Appl. No. 09/287,632, filed Apr. 7, 1999.
Amendment submitted May 10, 2006, in connection with U.S. Appl. No. 09/287,632, filed Apr. 7, 1999.
Interview Summary issued Jun. 2, 2006, in connection with U.S. Appl. No. 09/287,632, filed Apr. 7, 1999.
Office Action issued Jun. 22, 2006 in connection with U.S. Appl. No. 09/287,632, filed Apr. 7, 1999.
Petition to Correct Inventorship Pursuant to 37 C.F.R. 1.48(a) submitted Sep. 13, 2006 in connection with U.S. Appl. No. 09/287,632, filed Apr. 7, 1999.
Amendment submitted Nov. 22, 2006 in connection with U.S. Appl. No. 09/287,632, filed Apr. 7, 1999.
Office Action issued Feb. 8, 2007, in connection with U.S. Appl. No. 09/287,632, filed Apr. 7, 1999.

Amendment submitted Aug. 8, 2007, in connection with U.S. Appl. No. 09/287,632, filed Apr. 7, 1999.
Declaration of Dr. Elizabeth Salisbury Dennis Under Under 37 C.F.R. §1.132, including Exhibits 1 to 14 submitted Aug. 8, 2007 in connection with U.S. Appl. No. 09/287,632, filed Apr. 7, 1999.
Declaration of Dr. Marc De Block Under 37 C.F.R. §1.132, including Annexes 1 and 2 submitted Aug. 8, 2007, in connection with U.S. Appl. No. 09/287,632, filed Apr. 7, 1999.
Office Action issued Nov. 1, 2007, in connection with U.S. Appl. No. 09/287,632, filed Apr. 7, 1999.
Nov. 1, 2007 Declaration Under 37 C.F.R. § 1.131, including Exhibits 1 to 5 of Dr. Elizabeth Salisbury Dennis in connection with U.S. Appl. No. 09/287,632, filed Apr. 7, 1999.
Interview Summary issued Nov. 30, 2007 in connection with U.S. Appl. No. 09/287,632, filed Apr. 7, 1999.
Amendment submitted May 1, 2008 in connection with U.S. Appl. No. 09/287,632, filed Apr. 7, 1999.
May 1, 2008 Declaration Under 37 C.F.R. § 1.131, including Exhibits 1 to 5 of Peter Michael Waterhouse, Michael Wayne Graham, Ming-Bo Wang and Neil A. Smith in connection with U.S. Appl. No. 09/297,632, filed Apr. 7, 1999.
May 7, 2008 Declaration Under 37 C.F.R. 1.132 of Peter Robert Schofield Resubmission in connection with U.S. Appl. No. 09/287,632, filed Apr. 7, 1999.
Office Action issued Sep. 19, 2008 in connection with U.S. Appl. No. 09/287,632, filed Apr. 7, 1999.
Amendment submitted Mar. 19, 2009 in connection with U.S. Appl. No 09/287,632, filed Apr. 7, 1999.
Mar. 18, 2009 Declaration Under 37 C.F.R. 1.131 including Annexes I to III, of Dr. Michael Metzlaff in connection with U.S. Appl. No. 09/287,632, filed Apr. 7, 1999.
Office Action issued May 11, 2009 in connection with U.S. Appl. No. 09/287,632, filed Apr. 7, 1999.
Amendment submitted Nov. 5, 2009 in connection with U.S. Appl. No. 09/287,632, filed Apr. 7, 1999.
Office Action issued Dec. 8, 2009 in connection with U.S. Appl. No. 09/287,632, filed Apr. 7, 1999.
Appeal Brief submitted Apr. 8, 2010 in connection with U.S. Appl. No. 09/287,632, filed Apr. 7, 1999.
Claims pending as of Apr. 27, 2010 of U.S. Appl. No. 09/287,632, filed Apr. 7, 1999, particularly claims 63, 64, and 103.
Examiner's Answer issued Jul. 7, 2010 in connection with U.S. Appl. No. 09/287,632, filed Apr. 7, 1999.
Reply Brief submitted Sep. 7, 2010 in connection with U.S. Appl. No. 09/287,632, filed Apr. 7, 1999.
Amendment submitted Apr. 29, 2002 in connection with U.S. Appl. No. 09/100,812, filed Jun. 19, 1998.
Amendment submitted Nov. 10, 2000 in connection with U.S. Appl. No. 09/100,812, filed Jun. 19, 1998.
Amendment submitted Nov. 12, 2001 in connection with U.S. Appl. No. 09/100,812, filed Jun. 19, 1998.
Amendment submitted Oct. 17, 2002 in connection with U.S. Appl. No. 09/100,812, filed Jun. 19, 1998.
Amendment submitted Sep. 26, 2002 in connection with U.S. Appl. No. 09/100,812, filed Jun. 19, 1998.
Communication submitted Apr. 3, 2000 in connection with U.S. Appl. No. 09/100,812, filed Jun. 19, 1998.
Complete file history of U.S. Patent No. 6,573,099, Jun. 3, 2003 (U.S. Appl. No. 09/100,812, filed Jun. 19, 1998; Michael Wayne Graham and Robert Norman Rice).
Declaration of Kenneth Clifford Reed submitted Sep. 26, 2002 connection with U.S. Appl. No. 09/100,812, filed Jun. 19, 1998.
Declaration of Michael Wayne Graham submitted Apr. 29, 2002 in connection with U.S. Appl. No. 09/100,812, filed Jun. 19, 1998.
Declaration of Michael Wayne Graham submitted Sep. 26, 2002 in connection with U.S. Appl. No. 09/100,812, filed Jun. 19, 1998.
Interview Summery issued Jan. 11, 2001 in connection with U.S. Appl. No. 09/100,812, filed Jun. 19, 1998.
Interview Summary issued Sep. 18, 2002 in connection with U.S. Appl. No. 09/100,812, filed Jun. 19, 1998.

Notice of Allowability, including Examiner's Amendment and Examiner's Statement of Reasons for Allowance issued Nov. 20, 2002 in connection with U.S. Appl. No. 09/100,812, filed Jun. 19, 1998.
Office Action issued Dec. 2, 1999 in connection with U.S. Appl. No. 09/100,812, filed Jun. 19, 1998.
Office Action issued Feb. 12, 2001 in connection with U.S. Appl. No. 09/100,812, filed Jun. 19, 1998.
Office Action issued May 10, 2000 in connection with U.S. Appl. No. 09/100,812, filed Jun. 19, 1998.
Advisory Action issued Feb. 15, 2002 in connection with U.S. Appl. No. 09/100,812, filed Jun. 19, 1998.
Advisory Action issued Feb. 16, 2010 in connection with U.S. Appl. No. 11/179,504, filed Jul. 13, 2005.
Advisory Action issued Jun. 6, 2008 in connection with U.S. Appl. No. 11/179,504, filed Jul. 13, 2005.
Amendment as a Submission to Accompanying Request for Continued Examination submitted Apr. 19, 2010 in connection with U.S. Appl. No. 11/179,504, filed Jul. 13, 2005.
Amendment in Response to Dec. 16, 2010 Office Action submitted May 16, 2011 in connection with U.S. Appl. No. 11/179,504, filed Jul. 13, 2005.
Amendment submitted Feb. 15, 2008 in connection with U.S. Appl. No. 11/179,504, filed Jul. 13, 2005, including Exhibit A.
Amendment submitted Feb. 28, 2007 in connection with U.S. Appl. No. 11/179,504, filed Jul. 13, 2005.
Amendment submitted May 11, 2009 in connection with U.S. Appl. No. 11/179,504, filed Jul. 13, 2005.
Amendment submitted Oct. 18, 2007 in connection with U.S. Appl. No. 11/179,504, filed Jul. 13, 2005.
Amendment submitted Sep. 2, 2008 in connection with U.S. Appl. No. 11/179,504, filed Jul. 13, 2005.
Amendment, including Exhibits A and B submitted May 21, 2008 in connection with U.S. Appl. No. 11/179,504, filed Jul. 13, 2005.
Complete file history for U.S. Published Application No. 2005/0251877A1, published Nov. 10, 2005 (U.S. Appl. No. 11/179,504, filed Jul. 13, 2005; Peter Michael Waterhouse and Ming-Bo Wang).
Communication submitted Sep. 2, 2008 in connection with U.S. Appl. No. 11/179,504, filed Jul. 13, 2005.
Final Office Action issued Aug. 13, 2009 in connection with U.S. Appl. No. 11/179,504, filed Jul. 13, 2005.
Interview Summary for Feb. 1, 2008 Interview in connection with U.S. Appl. No. 11/179,504, filed Jul. 13, 2005.
Office Action issued Apr. 18, 2007 in connection with U.S. Appl. No. 11/179,504, filed Jul. 13, 2005.
Office Action issued Dec. 16, 2010 in connection with U.S. Appl. No. 11/179,504, filed Jul. 13, 2005.
Office Action issued Dec. 20, 2007 in connection with U.S. Appl. No. 11/179,504, filed Jul. 13, 2005.
Office Action issued Jan. 30, 2007 in connection with U.S. Appl. No. 11/179,504, filed Jul. 13, 2005.
Office Action issued Jul. 30, 2008 in connection with U.S. Appl. No. 11/179,504, filed Jul. 13, 2005.
Office Action issued Mar. 21, 2008 in connection with U.S. Appl. No. 11/179,504, filed Jul. 13, 2005.
Office Action issued Nov. 10, 2008 in connection with U.S. Appl. No. 11/179,504, filed Jul. 13, 2005.
Preliminary Amendment submitted Jul. 13, 2005 in connection with U.S. Appl. No. 11/179,504, filed Jul. 13, 2005.
Response submitted Feb. 3, 2010 in connection with U.S. Appl. No. 11/179,504, filed Jul. 13, 2005.
Advisory Action issued Jul. 20, 2007 in connection with U.S. Appl. No. 10/821,710, filed Apr. 8, 2004.
Advisory Action issued Sep. 14, 2005 in connection with U.S. Appl. No. 10/821,710, filed Apr. 8, 2004.
Amendment submitted Apr. 29, 2005 in connection with U.S. Appl. No. 10/821,710, filed Apr. 8, 2004.
Amendment submitted Aug. 29, 2005 in connection with U.S. Appl. No. 10/821,710, filed Apr. 8, 2004.
Amendment submitted Dec. 15, 2004 in connection with U.S. Appl. No. 10/821,710, filed Apr. 8, 2004.
Amendment submitted Feb. 7, 2008 in connection with U.S. Appl. No. 10/821,710, filed Apr. 8, 2004.

Amendment submitted Jul. 12, 2007 in connection with U.S. Appl. No. 10/821,710, filed Apr. 8, 2004.
Amendment submitted Jul. 25, 2007 in connection with U.S. Appl. No. 10/821,710, filed Apr. 8, 2004.
Amendment submitted Nov. 20, 2006 in connection with U.S. Appl. No. 10/821,710, filed Apr. 8, 2004.
Amendment submitted Oct. 31, 2007 in connection with U.S. Appl. No. 10/821,710, filed Apr. 8, 2004.
Complete file history for U.S. Published Application No. 2004/0237145 A1, published Nov. 25, 2004 (U.S. Appl. No. 10/821,710, filed Apr. 8, 2004; Michael Wayne Graham et al.).
Decision on Petition to Make Special Under 37 CFR 1.102(d) submitted Jul. 23, 2004 in connection with U.S. Appl. No. 10/821,710, filed Apr. 8, 2004.
Interview Summary issued Nov. 6, 2006 in connection with U.S. Appl. No. 10/821,710, filed Apr. 8, 2004.
Notice of Abandonment issued Dec. 15, 2008 in connection with U.S. Appl. No. 10/821,710, filed Apr. 8, 2004.
Office Action issued Apr. 17, 2008 in connection with U.S. Appl. No. 10/821,710, filed Apr. 8, 2004.
Office Action issued Aug. 7, 2007 in connection with U.S. Appl. No. 10/821,710, filed Apr. 8, 2004.
Office Action issued Feb. 11, 2005 in connection with U.S. Appl. No. 10/821,710, filed Apr. 8, 2004.
Office Action issued Feb. 8, 2005 in connection with U.S. Appl. No. 10/821,710, filed Apr. 8, 2004.
Office Action issued Jan. 12, 2007 in connection with U.S. Appl. No. 10/821,710, filed Apr. 8, 2004.
Office Action issued Jun. 19, 2006 in connection with U.S. Appl. No. 10/821,710, filed Apr. 8, 2004.
Office Action issued Jun. 29, 2005 in connection with U.S. Appl. No. 10/821,710, filed Apr. 8, 2004.
Office Action issued Oct. 15, 2004 in connection with U.S. Appl. No. 10/821,710, filed Apr. 8, 2004.
Petition to Make Special Under 37 CFR 1.102(d) submitted Jul. 23, 2004 in connection with U.S. Appl. No. 10/821,710, filed Apr. 8, 2004.
Preliminary Amendment submitted Dec. 21, 2005 in connection with U.S. Appl. No. 10/821,710, filed Apr. 8, 2004.
Request to Correct Inventorship Under 37 C.F.R. §1.48(a) submitted Dec. 12, 2007 in connection with U.S. Appl. No. 10/821,710, filed Apr. 8, 2004.
Amendment and Request for Continued Examination submitted Jan. 7, 2009 in connection with U.S. Appl. No. 10/346,853, filed Jan. 17, 2003.
Amendment in Response to Jan. 26, 2011 Office Action submitted Feb. 16, 2011 in connection with U.S. Appl. No. 10/346,853, filed Jan. 17, 2003.
Amendment in Response to May 15, 2009 Final Office Action as a Submission to Accompanying Request for Continued Examination submitted Oct. 15, 2009 in connection with U.S. Appl. No. 10/346,853, filed Jan. 17, 2003.
Amendment submitted Apr. 16, 2008 in connection with U.S. Appl. No. 10/346,853, filed Jan. 17, 2003.
Amendment submitted Dec. 27, 2006 in connection with U.S. Appl. No. 10/346,853, filed Jan. 17, 2003.
Amendment submitted Feb. 22, 2007, in connection with U.S. Appl. No. 10/346,853, filed Jan. 17, 2003.
Amendment submitted Jan. 17, 2003 in connection with U.S. Appl. No. 10/346,853, filed Jan. 17, 2003.
Amendment submitted Mar. 25, 2003 in connection with U.S. Appl. No. 10/346,853, filed Jan. 17, 2003.
Amendment submitted Oct. 17, 2007 in connection with U.S. Appl. No. 10/346,853, filed Jan. 17, 2003.
Aug. 4, 2011 Notice of Allowance issued in connection with U.S. Appl. No. 10/346,853, filed Jan. 7, 2003.
Communication submitted Aug. 2, 2005 in connection with U.S. Appl. No. 10/346,853, filed Jan. 17, 2003.
Complete file history for U.S. Published Application No. 2003/0159161 A1, published Aug. 21, 2003 (U.S. Appl. No. 10/346,853, filed Jan. 17, 2003; Michael Wayne Graham and Robert Norman Rice).

Decision on Petition to Make Special Under 37 CFR 1.102(d) submitted Jul. 27, 2004 in connection with U.S. Appl. No. 10/346,853, filed Jan. 17, 2003.
Final Office Action issued May 15, 2009 in connection with U.S. Appl. No. 10/346,853, filed Jan. 17, 2003.
Interview Summary issued Dec. 11, 2007 in connection with U.S. Appl. No. 10/346,853, filed Jan. 17, 2003.
Jan. 26, 2011 Office Action issued in connection with U.S. Appl. No. 10/346,853, filed Jan. 17, 2003.
May 13, 2011 Response to Apr. 19, 2011 Office Action submitted in connection with U.S. Appl. No. 10/346,853, filed Jan. 7, 2003.
Notice of Improper Request for Continued Examination issued Oct. 29, 2008 in connection with U.S. Appl. No. 10/346,853, filed Jan. 17, 2003.
Office Action issued Apr. 15, 2010 in connection with U.S. Appl. No. 10/346,853, filed Jan. 7, 2003.
Office Action issued Apr. 17, 2007 in connection with U.S. Appl. No. 10/346,853, filed Jan. 17, 2003.
Office Action issued Apr. 19, 2011 in connection with U.S. Appl. No. 10/346,853, filed Jan. 7, 2003.
Office Action issued Jan. 16, 2009 in connection with U.S. Appl. No. 10/346,853, filed Jan. 17, 2003.
Office Action issued Jul. 22, 2005 in connection with U.S. Appl. No. 10/346,853, filed Jan. 17, 2003.
Office Action issued Jul. 7, 2008 in connection with U.S. Appl. No. 10/346,853, filed Jan. 17, 2003.
Office Action issued Jun. 27, 2006 in connection with U.S. Appl. No. 10/346,853, filed Jan. 17, 2003.
Petition for Unintentionally Delayed Claim of Priority under 37 CFR § 1.78(a) (3) submitted Dec. 27, 2006 in connection with U.S. Appl. No. 10/346,853, filed Jan. 17, 2003.
Petition to Make Special Under 37 CFR 1.102(d) submitted Jul. 27, 2004 in connection with U.S. Appl. No. 10/346,853, filed Jan. 17, 2003.
Request for Continued Examination submitted Oct. 7, 2008 in connection with U.S. Appl. No. 10/346,853, filed Jan. 17, 2003.
Supplemental Amendment to Oct. 15, 2009 Amendment Filed in Response to May 15, 2009 Final Office Action, Summary of Examiner Interviews, and Supplemental Information Disclosure Statement submitted Dec. 21, 2009 in connection with U.S. Appl. No. 10/346,853, filed Jan. 17, 2003.
Amendment and Supplemental Information Disclosure Statement as a Submission Accompanying a Request for Continued Examination filed Dec. 15, 2010 in connection with U.S. Appl. No. 11/218,999, filed Sep. 2, 2005.
Amendment in Response to Oct. 9, 2009 Final Office Action as a Submission to Accompanying Request for Continued Examination submitted Mar. 9, 2010 in connection with U.S. Appl. No. 11/218,999, filed Sep. 2, 2005.
Amendment submitted Feb. 19, 2008 in connection with U.S. Appl. No. 11/218,999, filed Sep. 2, 2005.
Amendment submitted Jun. 17, 2008 in connection with U.S. Appl. No. 11/218,999, filed Sep. 2, 2005.
Amendment submitted Mar. 30, 2009 in connection with U.S. Appl. No. 11/218,999, filed Sep. 2, 2005.
Amendment submitted Oct. 31, 2007 in connection with U.S. Appl. No. 11/218,999, filed Sep. 2, 2005.
Communication issued May 21, 2009 in connection with U.S. Appl. No. 11/218,999, filed Sep. 2, 2005.
Complete file history for U.S. Published Application No. 2006/0014715, published Jan. 19, 2006 (U.S. Appl. No. 11/218,999, filed Sep. 2, 2005; Michael Wayne Graham et al.).
Office Action issued Apr. 21, 2010 in connection with U.S. Appl. No. 11/218,999, filed Sep. 2, 2005.
Office Action issued May 21, 2008 in connection with U.S. Appl. No. 11/218,999, filed Sep. 2, 2005.
Office Action issued Oct. 9, 2009 in connection with U.S. Appl. No. 11/218,999, filed Sep. 2, 2005.
Office Action issued Sep. 17, 2007 in connection with U.S. Appl. No. 11/218,999, filed Sep. 2, 2005.
Office Action issued Sep. 30, 2008 in connection with U.S. Appl. No. 11/218,999, filed Sep. 2, 2005.

Preliminary Amendment to the Accompanying Divisional Application Filed Under 37 C.F.R. §1.53, Submission of Sequence Listing and Information Disclosure Statement submitted Sep. 2, 2005 in connection with U.S. Appl. No. 11/219,999, filed Sep. 2, 2005.
Request to Correct Inventorship Under 37 C.F.R. §1.48(a) submitted Oct. 31, 2007 in connection with U.S. Appl. No. 11/218,999, filed Sep. 2, 2005.
Response to Communication submitted Jun. 22, 2009 in connection with U.S. Appl. No. 11/218,999, filed Sep. 2, 2005.
Sep. 9, 2011 Office Action issued in connection with U.S. Appl. No. 11/218,999, filed Sep. 2, 2005.
Supplemental Response to Mar. 30, 2009 Amendment Filed in Response to Sep. 30, 2008 Office Action filed Aug. 4, 2009 in connection with U.S. Appl. No. 11/218,999, filed Sep. 2, 2005.
Amendment in Response to Mar. 30, 2011 Office Action and Supplemental Information Disclosure Statement submitted Jun. 28, 2011 in connection with U.S. Appl. No. 10/759,841, filed Jan. 15, 2004.
Amendment submitted Apr. 15, 2008 in connection with U.S. Appl. No. 10/759,841, filed Jan. 15, 2004.
Amendment submitted Dec. 29, 2006 in connection with U.S. Appl. No. 10/759,841, filed Jan. 15, 2004.
Amendment submitted Feb. 21, 2007, in connection with U.S. Appl. No. 10/759,841, filed Jan. 15, 2004.
Amendment submitted Oct. 25, 2007 in connection with U.S. Appl. No. 10/759,841, filed Jan. 15, 2004.
Amendment submitted Oct. 31, 2006 in connection with U.S. Appl. No. 10/759,841, filed Jan. 15, 2004.
Amendment submitted Oct. 9, 2008 in connection with U.S. Appl. No. 10/759,841, filed Jan. 15, 2004.
Amendment submitted Sep. 24, 2009 in connection with U.S. Appl. No. 10/759,841, filed Jan. 15, 2004.
Aug. 10, 2011 Response to Aug. 9, 2011 Final Office Action submitted in connection with U.S. Appl. No. 10/759,841, filed Jan. 15, 2004.
Aug. 25, 2011 Notice of Allowance issued in issued in connection with U.S. Appl. No. 10/759,841, filed Jan. 15, 2004.
Aug. 9, 2011 Final Office Action issued in connection with U.S. Appl. No. 10/759,841, filed Jan. 15, 2004.
Complete file history for U.S. Published Application No. 2004/0180439 A1, pub. Sep. 16, 2004 (U.S. Appl. No. 10/759,841, filed Jan. 15, 2004; Michael Wayne Graham and Robert Norman Rice).
Dec. 9, 2010 Petition to Withdraw from issue Pursuant to 37 C.F.R. 1.313(c), including a Request for Continued Examination, Amendment, and Supplemental Information Disclosure Statement submitted in connection with U.S. Appl. No. 10/759,841, filed Jan. 15, 2004.
Examiner Interview Summary Record (PTOL-413) issued Apr. 15, 2010 in connection with U.S. Appl. No. 10/759,841, filed Jan. 15, 2004.
Interview Summary for Dec. 22, 2008 in connection with U.S. Appl. No 10/759,841, filed Jan. 15, 2004.
Interview Summary for Feb. 12, 2009 Interview in connection with U.S. Appl. No, 10/759,341, filed Jan. 15, 2004.
Interview Summary issued Dec. 11, 2007 in connection with U.S. Appl. No. 10/759,841, filed Jan. 15, 2004.
Jun. 15, 2010 Amendment in Response to Mar. 9, 2010 Office Action, Summary of Apr. 8, 2010 Examiner Interview, and Supplemental Information Disclosure Statement submitted in connection with U.S. Appl. No. 10/759,841, filed Jan. 15, 2004.
Mar. 30, 2011 Office Action issued in connection with U.S. Appl. No. 10/759,841, filed Jan. 15, 2004.
Office Action issued Apr. 25, 2007 in connection with U.S. Appl. No. 10/759,841, filed Jan. 15, 2004.
Office Action issued Jan. 22, 2009 in connection with U.S. Appl. No. 10/759,841, filed Jan. 15, 2004.
Office Action issued Jan. 6, 2009 in connection with U.S. Appl. No. 10/759,841, filed Jan. 15, 2004.
Office Action issued Jan. 8, 2008 in connection with U.S. Appl. No. 10/759,841, filed Jan. 15, 2004.
Office Action issued Jul. 31, 2006 in connection with U.S. Appl. No. 10/759,841, filed Jan. 15, 2004.
Office Action issued Jul. 9, 2008 in connection with U.S. Appl. No. 10/759,841, filed Jan. 15, 2004.
Office Action issued Mar. 9, 2010 in connection with U.S. Appl. No. 10/759,841, filed Jan. 15, 2004.

Office Action issued Nov. 29, 2006 in connection with U.S. Appl. No. 10/759,841, filed Jan. 15, 2004.
Preliminary Amendment submitted Jan. 15, 2004 in connection with U.S. Appl. No. 10/759,841, filed Jan. 15, 2004.
Sep. 1, 2010 Notice of Allowance issued in connection with U.S. Appl. No. 10/759,841, filed Jan. 15, 2004.
Supplemental Amendment to Sep. 24, 2009 Amendment, Summary of Dec. 17, 2009 Examiner Interview, and Supplemental Information Disclosure Statement submitted Dec. 21, 2009 in connection with U.S. Appl. No. 10/759,841, filed Jan. 15, 2004.
Amendment issued Jan. 24, 2008 in connection with U.S. Appl. No. 10/646,070, filed Aug. 22, 2003.
Amendment submitted Apr. 7, 2005 in connection with U.S. Appl. No. 10/646,070, filed Aug. 22, 2003.
Amendment submitted Aug. 11, 2006 in connection with U.S. Appl. No. 10/646,070, filed Aug. 22, 2003.
Amendment submitted Dec. 15, 2004 in connection with U.S. Appl. No. 10/646,070, filed Aug. 22, 2003.
Amendment submitted Dec. 27, 2005 in connection with U.S. Appl. No. 10/646,070, filed Aug. 22, 2003.
Amendment submitted Feb. 28, 2007 in connection with U.S. Appl. No. 10/646,070, filed Aug. 22, 2003.
Amendment submitted Jul. 15, 2009 in connection with U.S. Appl. No. 10/646,070, filed Jul. 13, 2005.
Amendment submitted Jul. 24, 2006 in connection with U.S. Appl. No. 10/646,070, filed Aug. 22, 2003.
Amendment submitted Jul. 24, 2008 in connection with U.S. Appl. No. 10/646,070, filed Aug. 22, 2003.
Amendment submitted Jun. 22, 2006 in connection with U.S. Appl. No. 10/646,070, filed Aug. 22, 2003.
Amendment submitted May 11, 2009 in connection with U.S. Appl. No. 10/646,070, filed Jul. 13, 2005.
Amendment submitted Oct. 10, 2008 in connection with U.S. Appl. No. 10/646,070, filed Aug. 22, 2003.
Amendment submitted Oct. 29, 2007 in connection with U.S. Appl. No. 10/646,070, filed Aug. 22, 2003.
Amendment, including Exhibits A to I submitted Jul. 24, 2008 in connection with U.S. Appl. No. 10/646,070, filed Aug. 22, 2003.
Complete file history for U.S. Published Application No. 2004/0064842 A1, Apr. 1, 2004 (U.S. Appl. No. 10/646,070, filed Aug. 22, 2003; Michael Wayne Graham and Robert Norman Rice).
Decision on Petition to Make Special Under 37 CFR 1.102(d) submitted Jul. 27, 2004 in connection with U.S. Appl. No. 10/646,070, filed Aug. 22, 2003.
Interview Summary issued Dec. 11, 2007 in connection with U.S. Appl. No. 10/646,070, filed Aug. 22, 2003.
Issue Notification issued Jun. 23, 2010 in connection with U.S. Appl. No. 10/646,070, filed Aug. 22, 2003.
Notice of Allowability issued Jan. 27, 2010 in connection with U.S. Appl. No. 10/646,070, filed Aug. 22, 2003.
Notice to Comply with Requirements for Patent Applications Containing Nucleotide Sequence and/or Amino Acid Protein Sequence Disclosures issued Oct. 27, 2005 in connection with U.S. Appl. No. 10/646,070, filed Aug. 22, 2003.
Office Action issued Apr. 27, 2007 in connection with U.S. Appl. No. 10/646,070, filed Aug. 22, 2003.
Office Action issued Aug. 11, 2006 in connection with U.S. Appl. No. 10/646,070, filed Aug. 22, 2003.
Office Action issued Aug. 28, 2006 in connection with U.S. Appl. No. 10/646,070, filed Aug. 22, 2003.
Office Action issued Jul. 24, 2006 in connection with U.S. Appl. No. 10/646,070, filed Aug. 22, 2003.
Office Action issued Nov. 4, 2008 in connection with U.S. Appl. No. 10/646,070, filed Aug. 22, 2003.
Office Action issued Oct. 15, 2004 in connection with U.S. Appl. No. 10/646,070, filed Aug. 22, 2003.
Office Action, issued Jun. 9, 2009 in connection with U.S. Appl. No. 10/646,070, filed Jul. 13, 2005.
Petition to Make Special Under 37 CFR 1.102(d) submitted Jul. 27, in connection with U.S. Appl. No. 10/646,070, filed Aug. 22, 2003.
Preliminary Amendment submitted Aug. 22, 2003 in connection with U.S. Appl. No. 10/646,070, filed Aug. 22, 2003.

Supplemental Information Disclosure Statement submitted Apr. 27, 2010 in connection with U.S. Appl. No. 10/646,070, filed Aug. 22, 2003.
Terminal Disclaimer submitted Dec. 14, 2009 in connection with U.S. Appl. No. 10/646,070, filed Jul. 13, 2005.
Terminal Disclaimer submitted Nov. 11, 2009 in connection with U.S. Appl. No. 10/646,070, filed Jul. 13, 2005.
Amendment submitted Apr. 15, 2009, in connection with U.S. Appl. No. 11/364,183, filed Mar. 1, 2006.
Amendment submitted Jan. 10, 2008 in connection with U.S. Appl. No. 11/364,183, filed Mar. 1, 2006.
Amendment submitted Jul. 2, 2008 in connection with U.S. Appl. No. 11/364,183, filed Mar. 1, 2006.
Complete file history for U.S. Patent Publication No. 2006-0178335, published Aug. 10, 2006 (U.S. Appl. No. 11/364,183, filed Mar. 1, 2006; Peter Michael Waterhouse et al.).
Declaration by Dr. Michael Metzlaff Under 37 C.F.R. § 1.132 submitted Apr. 15, 2009, in connection with U.S. Appl. No. 11/364,183, filed Mar. 1, 2006.
Declaration of Geoffrey Ellacott submitted Apr. 15, 2009, in connection with U.S. Appl. No. 11/364,183, filed Mar. 1, 2006.
Declaration of Neil Smith submitted Apr. 15, 2009, in connection with U.S. Appl. No. 11/364,183, filed Mar. 1, 2006.
Declaration of Peter Michael Waterhouse submitted Apr. 15, 2009, in connection with U.S. Appl. No. 11/364,183, filed Mar. 1, 2006.
Interview Summary for Feb. 1, 2008 Interview in connection with U.S. Appl. No. 11/364,183, filed Mar. 1, 2006.
Interview Summary from Feb. 11, 2009 Interview in connection with U.S. Appl. No. 11/364,183, filed Mar. 1, 2006.
Jul. 2, 2008 Declaration Under 37 C.F.R. § 1.131, including Exhibits 1 to 3 of Peter Michael Waterhouse, Michael Wayne Graham, and Ming-Bo Wang in connection with U.S. Appl. No. 11/364,183, filed Mar. 1, 2006.
Jun. 17, 2010 Declaration of Interference issued in connection with U.S. Appl. No. 11/364,183, filed Mar. 1, 2006.
Office Action issued Apr. 17, 2008 in connection with U.S. Appl. No. 11/364,183, filed Mar. 1, 2006.
Office Action issued Jul. 10, 2007 in connection with U.S. Appl. No. 11/364,183, filed Mar. 1, 2006.
Office Action issued Nov. 4, 2009 in connection with U.S. Appl. No. 11/364,183, filed Mar. 1, 2006.
Office Communication issued Jun. 11, 2010 in connection with U.S. Appl. No. 11/364,193, filed Mar. 1, 2006.
Office Communication issued Jun. 8, 2010 in connection with U.S. Appl. No. 11/364,183, filed Mar. 1, 2006.
Preliminary Amendment submitted Mar. 1, 2006 in connection with U.S. Appl. No. 11/364,183, filed Mar. 1, 2006.
Redeclaration of Interference issued Jul. 6, 2010 in connection with U.S. Appl. No. 11/364,183, filed Mar. 1, 2006.
Redeclaration of Interference issued Nov. 17, 2010 in connection with U.S. Appl. No. 11/364,183, filed Mar. 1, 2006.
Redeclaration of Interference issued Sep. 10, 2010 in connection with U.S. Appl. No. 11/364,183, filed Mar. 1, 2006.
Reply to the Nov. 4, 2009 Office Action submitted May 4, 2010 in connection with U.S. Appl. No. 11/364,183, filed Mar. 1, 2006.
Revised Amendment and Reply submitted Aug. 10, 2009 in connection with U.S. Appl. No. 11/364,183, filed Mar. 1, 2006.
Suggestion of Interference Pursuant to 37 C.F.R. § 41.202, submitted Apr. 15, 2009, in connection with U.S. Appl. No. 11/364,183, filed Mar. 1, 2006.
Amendment submitted Apr. 7, 2006 in connection with U.S. Appl. No. 10/152,808, filed May 23, 2002.
Amendment submitted Jul. 13, 2005, including Terminal Disclaimer in connection with U.S. Appl. No. 10/152,808, filed May 23, 2002.
Amendment submitted Oct. 22, 2004 in connection with U.S. Appl. No. 10/152,608, filed May 23, 2002.
Complete file history for U.S. Patent No. 7,138,565 B2, issued Nov. 21, 2006 (U.S. Appl. No. 10/152,808, filed May 23, 2002; Peter Michael Waterhouse and Ming-Bo Wang).
Notice of Allowability, including Examiner's Statement of Reasons Allowance issued Jul. 11, 2006 in connection with U.S. Appl. No. 10/152,808, filed May 23, 2002.
Office Action issued Jan. 13, 2005 in connection with U.S. Appl. No. 10/152,808, filed May 23, 2002.
Office Action issued Oct. 7, 2005 in connection with U.S. Appl. No. 10/152,808, filed May 23, 2002.
Office Action issued Sep. 22, 2004 in connection with U.S. Appl. No. 10/152,808, filed May 23, 2002.
Preliminary Amendment submitted May 23, 2002 in connection with U.S. Appl. No. 10/152,808, filed May 23, 2002.
Amendment submitted Dec. 18, 2002 in connection with U.S. Appl. No. 09/646,807, filed Dec. 5, 2000.
Amendment submitted Dec. 27, 2005 in connection with U.S. Appl. No. 09/646,807, filed Dec. 5, 2000.
Amendment submitted Dec. 28, 2006 in connection with U.S. Appl. No. 09/646,807, filed Dec. 5, 2000.
Amendment submitted Dec. 7, 2004 in connection with U.S. Appl. No. 09/646,807, filed Dec. 5, 2000.
Amendment submitted Mar. 10, 2005 in connection with U.S. Appl. No. 09/646,807, filed Dec. 5, 2000.
Amendment submitted Sep. 8, 2003 in connection with U.S. Appl. No. 09/646,807, filed Dec. 5, 2000.
Communication issued Feb. 17, 2005 in connection with U.S. Appl. No. 09/646,807, filed Dec. 5, 2000.
Communication issued Oct. 27, 2005 in connection with U.S. Appl. No. 09/646,807, filed Dec. 5, 2000.
Office Action issued Dec. 17, 2003 in connection with U.S. Appl. No. 09/646,807, filed Dec. 5, 2000.
Office Action issued Jul. 8, 2008 in connection with U.S. Appl. No. 09/646,807, filed Dec. 5, 2000.
Office Action issued Jun. 28, 2006 in connection with U.S. Appl. No. 09/646,807, filed Dec. 5, 2000.
Office Action issued Mar. 7, 2003 in connection with U.S. Appl. No. 09/646,807, filed Dec. 5, 2000.
Office Action issued Nov. 18, 2002 in connection with U.S. Appl. No. 09/646,807, filed Dec. 5, 2000.
Petition for Unintentionally Delayed Claim of Priority under 37 § 1.78(a) (3) submitted Dec. 28, 2006 in connection with U.S. Appl. No. 09/646,807, filed Dec. 5, 2000.
Preliminary Amendment submitted Jul. 30, 2001 in connection with U.S. Appl. No. 09/646,807, filed Dec. 5, 2000.
Preliminary Amendment submitted May 14, 2001 in connection with U.S. Appl. No. 09/646,807, filed Dec. 5, 2000.
Preliminary Amendment submitted Sep. 20, 2000 in connection with U.S. Appl. No. 09/646,807, filed Dec. 5, 2000.
Request to Correct Inventorship Under 37 C.F.R. §1.48(a) submitted Dec. 12, 2007 in connection with U.S. Appl. No. 09/646,807, filed Dec. 5, 2000.
U.S. Appl. No. 09/646,807, filed Dec. 5, 2000 (Michael Wayne Graham et al.).
Amendment submitted Dec. 19, 2008 in connection with U.S. Appl. No. 10/571,384, filed Jun. 1, 2006.
Amendment submitted Feb. 8, 2007 in connection with U.S. Appl. No. 10/571,384, filed as a §371 national stage of PCT International Application No. PCT/AU2004/01237.
Amendment submitted Jul. 15, 2009 in connection with U.S. Appl. No. 10/571,384, filed Jun. 1, 2006.
Complete file history for U.S. Patent Publication No. 2008/0044906 A1, published Feb. 21, 2008 (U.S. Appl. No. 10/571,384, filed Jun. 1, 2006; Peter Michael Waterhouse et al.).
Office Action issued Jan. 15, 2009 in connection with U.S. Appl. No. 10/571,384, filed Jun. 1, 2006.
Office Action issued Jun. 19, 2008 in connection with U.S. Appl. No. 10/571,384, filed Jun. 1, 2006.
Office Action issued Oct. 1, 2009 in connection with U.S. Appl. No. 10/571,384, filed Jun. 1, 2006.
Preliminary Amendment submitted Mar. 10, 2006 in connection with U.S. Appl. No. 10/571,384, filed as a §371 national stage of PCT International Application No. PCT/AU2004/01237.
U.S. Appl. No. 10/571,384, filed Sep. 10, 2004.
Amendment submitted Dec. 22, 2006, in connection with U.S. Appl. No. 11/180,928, filed Jul. 13, 2005.
Amendment submitted Jun. 6, 2008 in connection with U.S. Appl. No. 11/180,928, filed Jul. 13, 2005.

Amendment submitted Oct. 17, 2007 in connection with U.S. Appl. No. 11/180,928, filed Jul. 13, 2005.
Communication submitted Mar. 6, 2007 in connection with U.S. Appl. No. 11/180,928, filed Jul. 13, 2005.
Complete file history for U.S. Published Application No. 2005/0250208 A1, pub. Nov. 10, 2005 (U.S. Appl. No. 11/180,928, filed Jul. 13, 2005; Michael Wayne Graham et al.).
Interview Summary issued Dec. 11, 2007 in connection with U.S. Appl. No. 11/180,928, filed Jul. 13, 2005.
Office Action issued Apr. 17, 2007 in connection with U.S. Appl. No. 11/180,928, filed Jul. 13, 2005.
Office Action issued Feb. 6, 2007 in connection with U.S. Appl. No. 11/180,928, filed Jul. 13, 2005.
Office Action issued Jan. 8, 2008 in connection with U.S. Appl. No. 11/180,928, filed Jul. 13, 2005.
Office Action issued Oct. 31, 2006 in connection with U.S. Appl. No. 11/180,928, filed Jul. 13, 2005.
Preliminary Amendment submitted Jul. 13, 2005 in connection with U.S. Appl. No. 11/180,928, filed Jul. 13, 2005.
Request to Correct Inventorship Under 37 C.F.R. §1.48(a) filed Oct. 17, 2007 in connection with U.S. Appl. No. 11/180,928, filed Jul. 13, 2005.
Amendment submitted Dec. 23, 2009 in connection with U.S. Appl. No. 11/593,056, filed Nov. 6, 2006.
Amendment submitted Jun. 12, 2008 in connection with U.S. Appl. No. 11/593,056, filed Nov. 6, 2006.
Amendment submitted Mar. 12, 2009 in connection with U.S. Appl. No. 11/593,056, filed Nov. 6, 2006.
Communication submitted Sep. 21, 2007 in connection with U.S. Appl. No. 11/593,056, filed Nov. 6, 2006.
Final Office Action issued Mar. 24, 2010 in connection with U.S. Appl. No. 11/593,056, filed Nov. 6, 2006.
Office Action issued Dec. 12, 2007 in connection with U.S. Appl. No. 11/593,056, filed Nov. 6, 2006.
Office Action issued Jul. 24, 2007 in connection with U.S. Appl. No. 11/593,056, filed Nov. 6, 2006.
Office Action issued Jun. 24, 2009 in connection with U.S. Appl. No. 11/593,056, filed Nov. 6, 2006.
Office Action issued Sep. 12, 2008 in connection with U.S. Appl. No. 11/593,056, filed Nov. 6, 2006.
Preliminary Amendment submitted Nov. 6, 2006 in connection with U.S. Appl. No. 11/593,056, filed Nov. 6, 2006.
Amendment submitted Feb. 12, 2010 in connection with U.S. Appl. No. 11/841,737, filed Aug. 20, 2007.
Amendment submitted Jan. 16, 2008 in connection with U.S. Appl. No. 11/841,737, filed Aug. 20, 2007.
Amendment submitted Jul. 6, 2009 in connection with U.S. Appl. No. 11/841,737, filed Aug. 20, 2007.
Complete history for U.S. Patent Publication No 2008-0104732 A1, published May 1, 2008 (U.S. Appl. No. 11/841,737, filed Aug. 20, 2007; Peter Michael Waterhouse et al.).
Final Rejection issued Apr. 23, 2010 in connection with U.S. Appl. No. 11/841,737, filed Aug. 20, 2007.
Non-Final Rejection issued Aug. 12, 2009 in connection with U.S. Appl. No. 11/841,737, filed Aug. 20, 2007.
Notice of Publication issued May 1, 2008 in connection with U.S. Appl. No. 11/841,737, filed Aug. 20, 2007.
Restriction Requirement issued May 4, 2009 in connection with U.S. Appl. No. 11/841,737, filed Aug. 20, 2007.
Amendment submitted Jan. 30, 2009 in connection with U.S. Appl. No. 11/607,062, filed Dec. 1, 2006.
Complete file history for U.S. Patent Publication No. 2007-0078105, published Apr. 4, 2007 (U.S. Appl. No. 11/607,062, filed Dec. 1, 2006; Peter Michael Waterhouse et al.).
Office Action issued Jul. 31, 2008 in connection with U.S. Appl. No. 11/607,062, filed Dec. 1, 2006.
Office Action issued May 12, 2009 in connection with U.S. Appl. No. 11/607,062, filed Dec. 1, 2006.
Preliminary Amendment submitted Dec. 1, 2006 in connection with U.S. Appl. No. 11/607,062, filed Dec. 1, 2006.
Appeal Brief filed on Mar. 6, 2009 in U.S. Appl. No. 10/805,804.
Complete file history for U.S. Patent No. 6,423,885 B1, issued Jul. 23, 2002 (U.S. Appl. No. 09/373,720, filed Aug. 13, 1999; Peter Michael Waterhouse and Ming-Bo Wang).
Complete file history for U.S. Patent Publication No. 2004-0214330, published Oct. 28, 2004 (U.S. Appl. No. 10/755,328, filed Jan. 13, 2004; Peter Michael Waterhouse et al.).
Complete file history for U.S. Published Application No. 2003/074684 A1, published Apr. 17, 2003 (U.S. Appl. No. 09/997,905, filed Nov. 30, 2001; Michael Wayne Graham and Robert Norman Rice).
Jun. 22, 2011 Office Action issued in connection with Reexamination Control No. 90/009,722, filed Apr. 12, 2010.
Office Action issued Sep. 30, 2010 in connection with Reexamination Control No. 90/009,722, filed Apr. 12, 2010.
Office Communication Issued Mar. 11, 2011 in connection with Reexamination Control No. 90/009,722, filed Apr. 12, 2010.
Supplemental Amendment and Statement of the Substance of Interview submitted Apr. 8, 2011 in connection with Reexamination Control No. 90/009,722, filed Apr. 12, 2010.
Order Granting Request for Ex Parte Reexamination, issued May 13, 2010 in connection with Reexamination Control No. 90/009,722, filed Apr. 12, 2010.
Notice of Assignment of Reexamination Request, issued Apr. 20, in connection with Reexamination Control No. 90/009,722, filed Apr. 12, 2010.
Notice of Reexamination Request Filing Date, issued Apr. 20, 2010 in connection with Reexamination Control No. 90/009,722, filed Apr. 12, 2010.
Nov. 30, 2010 Amendment submitted in connection with Reexamination Control No. 90/009,722, filed Apr. 12, 2010.
Office Action issued Sep. 1, 2005 in connection with U.S. Appl. No. 10/755,328, filed Jan. 13, 2004.
Preliminary Amendment submitted Jan. 13, 2004 in connection with U.S. Appl. No. 10/755,328, filed Jan. 13, 2004.
Reply Brief to Examiner's Answer filed on Aug. 26, 2009, U.S. Appl. No. 10/805,804.
Request for Ex Parte Reexamination of U.S. Patent No. 7,138,565, including Exhibits A-K, submitted Apr. 9, 2010.
Oct. 31, 2005 Restriction Requirement in connection with U.S. Appl. No. 10/482,888, filed Jun. 14, 2004.
Jan. 3, 2006 Response to Oct. 31, 2005 Restriction Requirement in connection with U.S. Appl. No. 10/482,888, filed Jun. 14, 2004.
Jan. 13, 2006 Notice of Non-Compliant Amendment in connection with U.S. Appl. No. 10/482,888, filed Jun. 14, 2004.
Jan. 31, 2006 Response to Notice of Non-Compliant Amendment in connection with U.S. Appl. No. 10/482,888, filed Jun. 14, 2004.
May 19, 2006 Office Action in connection with U.S. Appl. No. 10/482,888, filed Jun. 14, 2004.
Oct. 23, 2006 Amendment in Response to May 19, 2006 Office Action in connection with U.S. Appl. No. 10/482,888, filed Jun. 14, 2004.
Jan. 8, 2007 Restriction Requirement in connection with U.S. Appl. No. 10/482,888, filed Jun. 14, 2004.
Feb. 12, 2007 Amendment in Response to Jan. 8, 2007 Restriction Requirement in connection with U.S. Appl. No. 10/482,888, filed Jun. 14, 2004.
May 1, 2007 Final Office Action in connection with U.S. Appl. No. 10/482,888, filed Jun. 14, 2004.
May 15, 2007 Amendment in Response to May 1, 2007 Final Office Action in connection with U.S. Appl. No. 10/482,888, filed Jun. 14, 2004.
Jun. 1, 2007 Advisory Action in connection with U.S. Appl. No. 10/482,888, filed Jun. 14, 2004.
Jul. 11, 2007 Advisory Action in connection with U.S. Appl. No. 10/482,888, filed Jun. 14, 2004.
Aug. 28, 2007 Amendment in Response to May 1, 2007 Final Office Action in connection with U.S. Appl. No. 10/482,888, filed Jun. 14, 2004.
Nov. 14, 2007 Office Action in Connection with U.S. Appl. No. 10/482,888, filed Jun. 14, 2004.
May 14, 2008 Response to Nov. 14, 2007 Office Action in connection with U.S. Appl. No. 10/482,888, filed Jun. 14, 2004.

Aug. 13, 2008 Final Office Action in connection with U.S. Appl. No. 10/482,888, filed Jun. 14, 2004.
Aug. 17, 2009 Amendment in connection with U.S. Appl. No. 10/482,888, filed Jun. 14, 2004.
Sep. 9, 2009 Supplemental Response to Aug. 17, 2009 Amendment in connection with U.S. Appl. No. 10/482,888, filed Jun. 14, 2004.
Sep. 25, 2009 Second Supplemental Response to Aug. 17, 2009 Amendment in connection with U.S. Appl. No. 10/482,888, filed Jun. 14, 2004.
Dec. 30, 2009 Office Action in connection with U.S. Appl. No. 10/482,888, filed Jun. 14, 2004.
Jun. 30, 2010 Communication in Response to Dec. 30, 2009 Office Action in connection with U.S. Appl. No. 10/482,888, filed Jun. 14, 2004.
Sep. 22, 2010 Final Office Action in connection with U.S. Appl. No. 10/482,888, filed Jun. 14, 2004.
Feb. 22, 2011 Amendment in Response to Sep. 22, 2010 Final Office Action in connection with U.S. Appl. No. 10/482,888, filed Jun. 14, 2004.
Apr. 18, 2011 Office Action in connection with U.S. Appl. No. 10/482,888, filed Jun. 14, 2004.
Sep. 19, 2011 Response to Apr. 18, 2011 Office Action in connection with U.S. Appl. No. 10/482,888, filed Jun. 14, 2004.
October 27, 2011 Notice of Allowance issued in connection with U.S. Appl. No. 10/482,888, filed Jun. 14, 2004.
U.S. Appl. No. 13/458,704, filed Apr. 27, 2012, Graham et al.
U.S. Appl. No. 13/474,539, filed May 17, 2012, Waterhouse et al.
Examiner's Report, issued Feb. 7, 2012 by the Canadian Patent Office in connection with counterpart Canadian Patent Application No. 2,455,490.
Response to European Search Opinion filed Dec. 15, 2011 with the European Patent Office in connection with counterpart European Patent Application No. 10184533.7.
Apr. 5, 2012 Communication from the Examining Division in connection with counterpart European Patent Application No. 02748428.6.
Jun. 12, 2012 Communication from the Examining Division in connection with counterpart European Patent Application No. 10184533.7.
Mar. 1, 2012 Office Action, issued in connection with U.S. Appl. No. 13/243,413.
Apr. 2, 2012 Response to Office Action, filed in connection with U.S. Appl. No. 13/243,413.
May 24, 2012 Notice of Allowance, issued in connection with U.S. Appl. No. 13/243,413.
Request for Further Processing and Response to a Communication from the Examining Division filed Feb. 1, 2013 in connection with related European Patent Application No. EP 02748428.0.

SEQUENCE LISTING

```
<160> NUMBER OF SEQ ID NOS: 6

<210> SEQ ID NO 1
<211> LENGTH: 27
<212> TYPE: DNA
<213> ORGANISM: Artificial
<220> FEATURE:
<223> OTHER INFORMATION: PCR primer

<400> SEQUENCE: 1
gaattcatgg tccgtcctgt agaaacc                                         27

<210> SEQ ID NO 2
<211> LENGTH: 24
<212> TYPE: DNA
<213> ORGANISM: Artificial
<220> FEATURE:
<223> OTHER INFORMATION: PCR primer

<400> SEQUENCE: 2
gaattccccc accgaggctg tagc                                            24

<210> SEQ ID NO 3
<211> LENGTH: 27
<212> TYPE: DNA
<213> ORGANISM: Artificial
<220> FEATURE:
<223> OTHER INFORMATION: PCR primer

<400> SEQUENCE: 3
gaattctaga atcccaaaac aaactgg                                         27

<210> SEQ ID NO 4
<211> LENGTH: 33
<212> TYPE: DNA
<213> ORGANISM: Artificial
<220> FEATURE:
<223> OTHER INFORMATION: PCR primer

<400> SEQUENCE: 4
ggatcctgac cgtccatcgc aataaaatga gcc                                  33

<210> SEQ ID NO 5
<211> LENGTH: 23
<212> TYPE: DNA
<213> ORGANISM: Artificial
<220> FEATURE:
```

```
<223> OTHER INFORMATION: PCR primer

<400> SEQUENCE: 5
ccgaaaatcc aatctacgga ccc                                               23

<210> SEQ ID NO 6
<211> LENGTH: 23
<212> TYPE: DNA
<213> ORGANISM: Artificial
<220> FEATURE:
<223> OTHER INFORMATION: PCR primer

<400> SEQUENCE: 6
cgacgaataa cctgggctgt tgc                                               23
```

DELIVERY OF DSRNA TO ARTHROPODS

This application is a continuation of U.S. Ser. No. 13/243,413, filed Sep. 23, 2011, now U.S. Pat. No. 8,263,573 which is a continuation of U.S. Ser. No. 10/482,888, filed Jun. 14, 2004, now U.S. Pat. No. 8,101,343, issued Jan. 24, 2012, a §371 national stage of PCT International Application No. PCT/AU02/00897, filed Jul. 5, 2002, which claims priority of Australian Application No. PR6215, filed Jul. 6, 2001, each of which are herein incorporated by reference in their entirety.

FIELD OF THE INVENTION

The present invention relates generally to dsRNA and its use in gene silencing. Furthermore, the present invention relates to methods of delivering dsRNA to an arthropod.

BACKGROUND OF THE INVENTION

RNA interference (RNAi) is considered as a naturally occurring adaptive defence in at least some organisms against viruses and the production of aberrant transcripts, such as those produced by transposon mobility (Bosher and Labouesse, 2000; Waterhouse et al., 2001).

The actual process by which dsRNA mediates target RNA degradation is not fully understood, but the cellular machinery involved is gradually being identified. Full-length dsRNAs have been observed to be progressively degraded into ~21-nucleotide dsRNAs, by an enzyme called Dicer-1 (Elbashir et al., 2001). It is believed that the Dicer-1 proteins, along with their associated 21-mer dsRNA, seek single stranded RNAs with sequence identity, and promote the cleavage of single stranded RNA targets (Waterhouse et al., 2001).

The intestine of *C. elegans* is a simple tube constructed of only 20 cells (White, 1988). For *C. elegans*, dsRNA has been microinjected into the gonadal tissues of adult worms, but simpler methods have since been developed that circumvent the tedious microinjection method. Nematodes fed *Escherichia coli* bacteria that simultaneously express sense and antisense RNAs can acquire dsRNA. Interestingly, the ingested dsRNA can then spread from the gut to target almost all tissues with the nematode (Timmons and Fire, 1998). Alternatively, the worms can be soaked in dsRNA solutions, either with liposomes or as naked RNA (Tabara et al., 1998; Maeda et al., 2001).

Arthropod guts are comprised of a great many cell types, and are highly variable, as they have adapted to the needs of each species and their unique dietary choices. The evolutionary distance between nematodes and insects is considerable, and there is no reason to assume that while feeding dsRNA to *C. elegans* was successful, it would be a technique easily transferable to insects. The presence of specific barriers in insect guts, such as the peritrophic membrane, could also limit or prevent direct absorption of orally delivered dsRNA. The midgut of an arthropod is the primary site of nutrient uptake, and midgut internal environments of different arthropods can vary widely. For example, the fruit fly *Drosophila melanogaster* has a rather acidic midgut lumen, while many Lepidoptera (moths and butterflies) have a very hostile, highly basic midgut environment.

SUMMARY OF THE INVENTION

The present invention provides methods that utilize dsRNA to determine the biological function of an RNA in an arthropod. In particular, the invention provides efficient mechanisms of delivering dsRNA to an arthropod with the aid of transfection promoting agents. Furthermore, the present invention provides methods for controlling pest arthropod populations, methods for controlling pathogens carried by arthropods, as well as methods for protecting an arthropod from a pathogen, parasite or predatory organism. In addition, the present invention provides transgenic organisms, in particular arthropods, expressing small dsRNA molecules.

In one aspect, the present invention provides a method of determining the biological function of a target RNA in an arthropod comprising delivering to the arthropod a dsRNA molecule which specifically reduces the level of the target RNA and/or the production of a protein encoded by the target RNA in a cell of the arthropod, and assessing the effect of the dsRNA on at least one biological function of the arthropod.

The method of the present invention can be utilized to rapidly screen uncharacterized RNAs or expressed sequence tags (ESTs) for a function(s), particularly in high(er) throughput screens of pest arthropod EST libraries. Ultimately, the method facilitates the identification of novel pesticide targets. For example, a particular dsRNA that confers lethality on an arthropod indicates that the corresponding RNA itself, or the protein encoded by a mRNA, is essential for arthropod survival, and, as a consequence, said RNA or protein is a good pesticide target. Accordingly, this RNA, or the protein encoded by the mRNA, is specifically targeted in the design of, and/or screening for, agents to control pest populations of the arthropod.

In an alternative embodiment, the method is used to determine any additional function(s) of previously characterized arthropod RNAs.

Alternatively, dsRNA is designed with specificity to an RNA that is potentially involved in particular biological processes (for example, determined by sequence identity with known genes, and/or through expression patterns) and can be screened to obtain a dsRNA that produces a particular phenotype. Such phenotypes include arthropod death or sterility. In fact, random dsRNA can be screened by this method for a desired phenotype.

Pathogens, such as viruses, which infect arthropods can be engineered to express a dsRNA for the down-regulation of a specific RNA. Typically, this would be for the production of biological agents to control a pest population of arthropods. However, such pathogens may not be easily manipulated, slowing down the progress of identifying suitable genetically engineered pathogens. The present invention can be used to rapidly screen candidate dsRNA molecules to determine if they produce the desired effect on a target arthropod pest. Once a candidate has been shown to produce the desired effect, suitable pathogens can be engineered and tested as biological control agents of an arthropod population.

The method of the invention can also be used to identify RNA important for enhancing production traits of an arthropod. In this instance, the activity of the dsRNA can down-regulate the production trait. Once identified, the relevant genes can be overexpressed to enhance these production traits. In accordance with this embodiment of the invention, the corresponding endogenous arthropod gene is ectopically expressed in the arthropod to enhance the production trait. Exemplary production traits contemplated herein include the composition and/or quantity of honey produced by bees, and the growth rate and/or size of edible crustaceans such as prawns, crayfish and lobsters, and the like.

In an alternate use of the method of the present invention, a target RNA can be assessed to determine whether it, or a protein encoded by the RNA, is acted upon by an agent such as a pesticide. In this instance, the method also comprises exposing the arthropod to the agent, wherein if the agent has little or no additional effect on the arthropod it indicates that the RNA, or protein encoded by the RNA, is directly acted upon by the agent or is involved in a biological pathway which is effected by the agent. Upon the identification of the mechanism of action of the agent, this information can be used to design alternate pesticides (for example) which act on the same molecules/pathways. This is particularly useful where an agent is known to be a potent pesticide, however, it is not approved for use due to concerns such as its toxicity to non-pest organisms.

In a preferred embodiment, the dsRNA is delivered by a process comprising contacting the arthropod with the dsRNA. Preferably, said contacting comprises wholly or partially soaking the arthropod in a composition comprising the dsRNA.

In a further preferred embodiment, the dsRNA is delivered by a process comprising feeding the dsRNA to the arthropod.

Preferably, the dsRNA is delivered in a composition comprising a transfection promoting agent. More preferably, the transfection promoting agent is a lipid-containing compound.

In one embodiment, the lipid-containing compound is selected from the group consisting of; Lipofectamine, Cellfectin, DMRIE-C, DOTAP and Lipofectin. In another embodiment, the lipid-containing compound is a Tris cationic lipid. Examples of suitable Tris cationic lipids include, but are not limited to, CS096, CS102, CS129, CS078, CS051, CS027, CS041, CS042, CS060, CS039, or CS015.

Preferably, the composition further comprises a nucleic acid condensing agent. The nucleic acid condensing agent can be any such compound known in the art. Examples of nucleic acid condensing agents include, but are not limited to, spermidine (N-[3-aminopropyl]-1,4-butanediamine), protamine sulphate, poly-lysine as well as other positively charged peptides. Preferably, the nucleic acid condensing agent is spermidine or protamine sulfate.

In yet another preferred embodiment, the composition further comprises buffered sucrose or phosphate buffered saline.

In an alternate embodiment, the dsRNA is delivered by a process comprising feeding a transgenic organism expressing the dsRNA to the arthropod. The transgenic organism is selected from, but not limited to, the group consisting of: plants, yeast, fungi, algae, bacteria or another arthropod expressing the dsRNA. Examples of suitable bacteria include *Pseudomonas fluorescens, E. coli, B. subtilis* (Gawron-Burke and Baum, 1991), and *Wolbachia* sp. Preferably, the transgenic organism is a transgenic plant.

In yet another embodiment, the dsRNA is delivered by a process comprising contacting the arthropod with a virus expressing the dsRNA.

Preferably, the dsRNA comprises a nucleotide sequence having at least 90% identity to at least a portion of the sequence of the target RNA, more preferably the dsRNA comprises a nucleotide sequence having at least 97% identity to at least a portion of the sequence of the target RNA, and even more preferably the dsRNA comprises a nucleotide sequence having at least 99% identity to at least a portion of the sequence of the target RNA.

The dsRNA has a region of self-complementarity to permit it assuming a double-stranded conformation in an arthropod host. Preferably, the region of self-complementary corresponds to at least about 20 to about 23 contiguous nucleotides of the target RNA, more preferably the full length sequence of the target RNA.

The arthropod can be any species. Preferably, the arthropod is of economic importance, such as, for example, an edible crustacean, an arthropod that causes disease, a household pest, an agricultural pest, or an arthropod that produces a useful substance or compound, such as, for example, silk, an edible substance (e.g. honey) or a medicinal substance or compound (e.g. a toxin or venom).

It is preferred that the arthropod is an insect or a crustacean. Most preferably the arthropod is an insect.

The arthropod can be at any stage of development, however, it is preferred that the arthropod is in a larval or adult developmental stage when the dsRNA is delivered. The present invention clearly encompasses determining the effect of the dsRNA on a phenotype of the arthropod at a later development stage even when the dsRNA is delivered at an earlier developmental stage.

Preferably, the RNA is mRNA.

In a further embodiment, the dsRNA molecule is designed based on the nucleotide sequence of an EST that has been derived from mRNA isolated from the arthropod.

In another aspect, the present invention provides a composition comprising dsRNA and a transfection promoting agent, wherein said dsRNA comprises a nucleotide sequence that it is at least 90% identical to the sequence of a target RNA, wherein the target RNA is selected from the group consisting of: a naturally-occurring arthropod RNA, a naturally-occurring RNA of an organism that is a pathogen carried by an arthropod, a naturally-occurring RNA of a virus that infects an arthropod, an RNA copy of a naturally-occurring DNA virus that infects an arthropod, and a naturally-occurring RNA of a bacterium that infects an arthropod.

It is preferred that the naturally occurring arthropod RNA is an mRNA which encodes a protein involved in, and more preferably essential for, arthropod development, neural function, reproduction or digestion.

Preferably, the transfection promoting agent is a lipid-containing compound.

In one embodiment, the lipid-containing compound is selected from the group consisting of; Lipofectamine, Cellfectin, DMRIE-C, DOTAP and Lipofectin. In another embodiment, the lipid-containing compound is a Tris cationic lipid. Examples of suitable Tris cationic lipids include, but are not to limited to, CS096, CS102, CS129, CS078, CS051, CS027, CS041, CS042, CS060, CS039, or CS015.

Preferably, the composition further comprises a nucleic acid condensing agent. The nucleic acid condensing agent can be any such compound known in the art. Examples include, but are not limited to, spermidine (N-[3-aminopropyl]-1,4-butanediamine), protamine sulphate, poly-lysine as well as other positively charged peptides. Preferably, the nucleic acid condensing agent is spermidine or protamine sulfate.

Preferably, the composition is formulated such that it can be applied to an area inhabited by a population of arthropods. This area can include crop plants, ornamental or native plants, or animals. Furthermore, the composition can be applied directly to an animal such as a cow or a sheep. Accordingly, in a preferred embodiment the composition further comprises an agriculturally acceptable carrier.

The composition of the present invention can also be formulated as a bait. In this instance, the composition further comprises a food substance and/or an attractant, such as a pheromone, to enhance the attractiveness of the bait to the arthropod.

In a further aspect, the present invention provides a method of controlling an arthropod pest comprising delivering to the arthropod dsRNA by a process comprising contacting the arthropod with said dsRNA or feeding said dsRNA to the arthropod, for a time and under conditions sufficient for said dsRNA, or a degradation product thereof, to specifically reduce the level of a target RNA and/or the production of a protein encoded by the target RNA in a cell of the arthropod, wherein the target RNA or the protein is important for arthropod survival, development and/or reproduction.

Preferably, the dsRNA is delivered in a composition according to the invention.

Preferably, the target RNA or the target protein is essential for arthropod development, neural function, reproduction or digestion.

The present invention is also used to control disease pathogens carried by arthropods. For instance, there are ecological arguments for not destroying mosquitoes to control malaria, sleeping sickness, and many arboviruses.

Accordingly, in yet another aspect, the present invention provides a method for controlling a pathogen transmitted by an arthropod, the method comprising delivering to the arthropod dsRNA by a process comprising contacting the arthropod with said dsRNA or feeding said dsRNA to said arthropod, for a time and under conditions sufficient for said dsRNA, or a degradation product thereof, to specifically reduce the level of a target RNA and/or the production of a protein encoded by the target RNA in a cell of the pathogen, wherein the target RNA or the protein is important for pathogen survival, development and/or reproduction.

Preferably, the dsRNA is delivered in a composition according to the invention.

In preferred embodiment of the third aspect, the pathogen is selected from the group consisting of fungi, protozoans, bacteria and viruses.

In the instance where the pathogen is a virus, the presence of the dsRNA, or degradation products thereof, in a cell of the arthropod specifically reduces the accumulation of a target RNA or the production of a protein essential for viral survival and/or replication.

Beneficial arthropods can be protected from parasite/pathogen attack by the delivery of appropriate dsRNA containing compositions. Insect colonies, in particular those such as bees, silkworms, or even laboratory stocks of insects, can be protected from parasitic or predatory pests (eg. nematodes, mites), or viral and microbial pathogens. Similarly, commercially important stocks of crustaceans can be protected from disease pathogens.

Thus, in a further aspect the present invention provides a method of protecting an arthropod against a pathogen, parasite or predatory organism, the method comprising delivering to the arthropod dsRNA by a process comprising contacting the arthropod with said dsRNA or feeding said dsRNA to said arthropod, for a time and under conditions sufficient for said dsRNA, or a degradation product thereof, to specifically reduce the level of a target RNA and/or the production of a protein encoded by the target RNA in a cell of the pathogen, parasite or predatory organism, wherein the target RNA or the protein is important for the survival, development and/or reproduction of the pathogen, parasite or predatory organism.

Preferably, the dsRNA is delivered in a composition according to the invention.

In the instance where the pathogen is a virus, the presence of the dsRNA, or degradation products thereof, in a cell of the arthropod specifically reduces the accumulation of RNA or the production of a protein essential for viral survival and/or replication.

Previously, dsRNA techniques have involved the use of constructs in which the dsRNA approximates the length of the entire open reading frame of a RNA or a substantial portion thereof. The present inventors have found that such long dsRNA constructs are not required in order to obtain RNA interference. Surprisingly, the present inventors have found that dsRNA as little as 21 nucleotides are capable of gene silencing. Furthermore, the present inventors have also surprisingly found that dsRNA that had been previously processed and partially degraded within one organism can still facilitate RNAi in another arthropod.

Hence, in another aspect the present invention provides a transgenic organism comprising a heterologous nucleic acid(s) which is transcribed to produce a dsRNA, wherein the portion of the dsRNA which is double stranded is about 21 to about 50 base pairs in length.

Preferably, the dsRNA comprises a nucleotide sequence having at least 90% identity to at least a portion of the sequence of a target RNA selected from the group consisting of: a naturally-occurring arthropod RNA, a naturally-occurring RNA of an organism that is a pathogen carried by an arthropod, a naturally-occurring RNA of a virus that infects an arthropod, an RNA copy of a naturally-occurring DNA virus that infects an arthropod, and a naturally-occurring RNA of a bacterium that infects an arthropod.

Preferably, the portion of the dsRNA which is double stranded is about 21 to about 23 base pairs in length.

Preferably, the organism is selected from the group consisting of: plants and arthropods.

In the instance where the transgenic organism is a plant, the dsRNA is preferably at least 90% identical to at least a portion of a RNA expressed in an arthropod which feeds on the plant.

Preferably, the dsRNA increases the resistance of the transgenic organism to a pathogen. Preferably, the pathogen is a virus.

Preferably, the dsRNA is produced as a single open reading frame in the transgenic organism, where the sense and anti-sense sequences are flanked by an unrelated sequence which enables the sense and anti-sense sequences to hybridize to form the dsRNA molecule with the unrelated sequence forming a loop structure.

As will be apparent, preferred features and characteristics of one aspect of the invention can be applicable to many other aspects of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

The invention will hereinafter be described by way of the following non-limiting Figures and Examples.

DETAILED DESCRIPTION OF THE INVENTION

General Techniques

Figure 1:
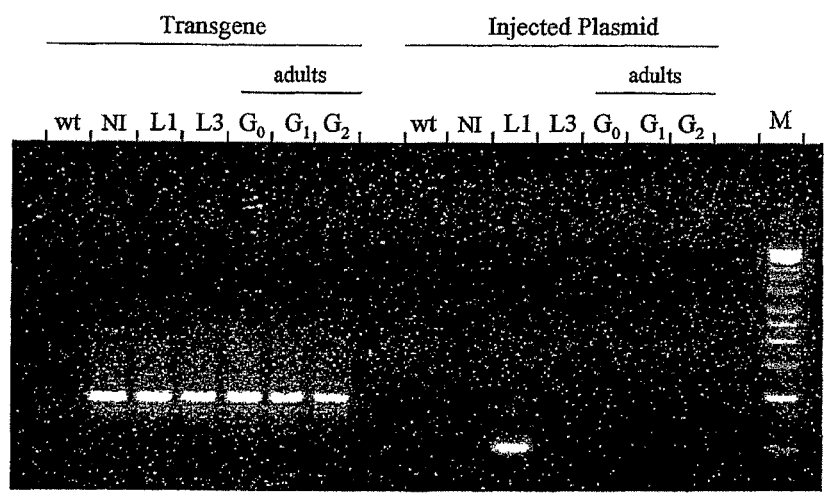
FIG. 1. PCR detection of phspGUS[i/r] plasmid in insects injected with the plasmid as late embryos. In the leftmost 7 lanes, the presence of the GUS transgene in the flies is evident by the production of the 1 kb PCR product in all developmental stages. There was no PCR product in wild type, non-transgenic flies (wt). In the right hand side of the gel, only L1 ($1^{st}$ instar larvae) show evidence of the injected plasmid, as indicated by the single 500 bp PCR product.

Unless otherwise indicated, the recombinant DNA techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (Editors), Current Protocols in Molecular Biology, Greene Pub. Associates and Wiley-Interscience (1988, including all updates until present) and are incorporated herein by reference.

Standard methods for the production of transgenic insects are outlined in "Insect Transgenesis—Methods and Applications" (Ed. A. M. Handler and A. A. James, CRC Press, London, 2000).

dsRNA

As used herein, "dsRNA" or "RNAi" refers to a polyribonucleotide structure formed either by a single self-complementary RNA strand or at least by two complementary RNA strands. The degree of complementary, in other words the % identity, need not necessarily be 100%. Rather, it must be sufficient to allow the formation of a double-stranded structure under the conditions employed.

Preferably, the % identity of a polyribonucleotide is determined by GAP (Needleman and Wunsch, 1970) analysis (GCG program) using the default settings, wherein the query sequence is at least about 21 to about 23 nucleotides in length, and the GAP analysis aligns the two sequences over a region of at least about 21 nucleotides. In another embodiment, the query sequence is at least 150 nucleotides in length, and the GAP analysis aligns the two sequences over a region of at least 150 nucleotides. In a further embodiment, the query sequence is at least 300 nucleotides in length and the GAP analysis aligns the two sequences over a region of at least 300 nucleotides. In yet another embodiment, the query sequence corresponds to the full length of the target RNA and the GAP analysis aligns the two sequences over the full length of the target RNA.

The design and production of suitable dsRNA molecules for the present invention is well within the capacity of a person skilled in the art, particularly considering Dougherty and Parks (1995), Waterhouse et al. (1998), Elbashir et al. (2001), WO 99/32619, WO 99/53050 and WO 99/49029.

Conveniently, the dsRNA can be produced from a single open reading frame in a recombinant host cell, wherein the sense and anti-sense sequences are flanked by an unrelated sequence which enables the sense and anti-sense sequences to hybridize to form the dsRNA molecule with the unrelated sequence forming a loop structure.

The two strands can also be expressed separately as two transcripts, one encoding the sense strand and one encoding the antisense strand.

RNA duplex formation can be initiated either inside or outside the cell. The dsRNA can be partially or fully double-stranded. The RNA can be enzymatically or chemically synthesized, either in vitro or in vivo.

The dsRNA need not be full length relative to either the primary transcription product or fully processed RNA. Generally, higher identity can be used to compensate for the use of a shorter sequence. Furthermore, the dsRNA can comprise single stranded regions as well, e.g., the dsRNA can be partially or fully double stranded. The double stranded region of the dsRNA can have a length of at least about 21 to about 23 base pairs, optionally a sequence of about 21 to about 50 base pairs, optionally a sequence of about 50 to about 100 base pairs, optionally a sequence of about 100 to about 200 base pairs, optionally a sequence of about 200 to about 500, and optionally a sequence of about 500 to about 1000 or more base pairs, up to molecule that is double stranded for its full length, corresponding in size to a full length target RNA molecule.

The dsRNA can contain known nucleotide analogs or modified backbone residues or linkages, which are synthetic, naturally occurring, and non-naturally occurring. Examples of such analogs include, without limitation, phosphorothioates, phosphoramidates, methyl phosphonates, chiralmethyl phosphonates and 2-O-methyl ribonucleotides.

As used herein, the term "specifically reduce the level of a target RNA and/or the production of a target protein encoded by the RNA", and variations thereof, refers to the sequence of a portion of one strand of the dsRNA being sufficiently identical to the target RNA such that the presence of the dsRNA in a cell reduces the steady state level and/or the production of said RNA. In many instances, the target RNA will be mRNA, and the presence of the dsRNA in a cell producing the mRNA will result in a reduction in the production of said protein. Preferably, this accumulation or production is reduced at least 10%, more preferably at least 50%, even more preferably at least 75%, yet even more preferably at least 95% and most preferably 100%, when compared to a wild-type cell.

The consequences of inhibition can be confirmed by examination of the outward properties of the cell or organism or by biochemical techniques such as, but not limited to, Northern hybridization, reverse transcription, gene expression monitoring with a microarray, antibody binding, enzyme linked immunosorbent assay (ELISA), Western blotting, radioimmunoassay (RIA), and other immunoassays.

Transfection Promoting Agent

Transfection promoting agents used to facilitate the uptake of nucleic acids into a living cell are well known within the art. Reagents enhancing transfection include chemical families of the types; polycations, dendrimers, DEAE Dextran, block copolymers and cationic lipids. Preferably, the transfection-promoting agent is a lipid-containing compound (or formulation), providing a positively charged hydrophilic region and a fatty acyl hydrophobic region enabling self-assembly in aqueous solution into vesicles generally known as micelles or liposomes, as well as lipopolyamines.

The formulation of polynucleotides encapsulated in lipid-containing compounds in known in the art and described in, for example, "Liposomes: from physical structure to therapeutic applications" (Ed. C. G. Knight. Elsevier Press, 1981).

As used herein;
1) CellFECTIN refers to a 1:1.5 (M/M) liposome formulation of the cationic lipid N,N',N'',N'''-tetramethyl-N,N',N'',N'''-tetrapalmitylspermine (TM-TPS) and dioleoyl phosphatidylethanolamine (DOPE) in membrane-filtered water;
2) Lipofectin refers to a 1:1 (w/w) liposome formulation of the cationic lipid N-[1-(2,3-dioleyloxy)propyl]-N,N,N-trimethylammonium chloride (DOTMA) and dioleoyl phosphatidylethanolamine (DOPE);
3) Lipofectamine refers to a 3:1 (w/w) liposome formulation of the polycationic lipid 2,3-dioleyloxy-N-[2(spermine-carboxamido)ethyl]-N,N-dimethyl-1-propanaminiumtrifluoroacetate (DOSPA) and the neutral lipid dioleoyl phosphatidylethanolamine (DOPE) in membrane-filtered water;
4) DMRIE-C refers to a 1:1 (M/M) liposome formulation of the cationic lipid DMRIE (1,2-dimyristyloxypropyl-3-dimethyl-hydroxy ethyl ammonium bromide) and cholesterol in membrane-filtered water;
5) DOTAP refers to cationic lipid N-[1-(2,3-dioleoyloxy)propyl]-N,N,N-trimethylammonium methyl-sulfate;
6) CS096: K3C10TChol (a T-shape trilysine head group with a C10 aliphatic spacer attached to a cholesterol hydrophobic domain via Tris molecule);
7) CS102: K3C10TL3 (T-shape trilysine with a C10 aliphatic spacer attached to three aliphatic fatty acid (C12) via Tris molecule);
8) CS129: K3C7TS3 (T-shape trilysine with a C7 aliphatic spacer attached to three aliphatic fatty acid (C18) via Tris molecule);
9) CS078: K2C10TL3 (dilysine with a C10 aliphatic spacer attached to threealiphatic fatty acid (C12) via Tris molecule);
10) CS051: K3GTL3 (tri-Lysine with a shorter Glycine spacer to three aliphatic fatty acid (C12) via Tris molecule);
11) CS027: KATP3 (monolysine with a short alanine spacer to three aliphatic fatty acid (C16) via Tris molecule);
12) CS041: K3ATL2 (trilysine with a short alanine spacer to two aliphatic fatty acid (C16) via Tris molecule);
13) CS042: K3ATL3 (trilysine with a short alanine spacer to three aliphatic fatty acid (C16) via Tris molecule);
14) CS060: K3C6TL3 (trilysine with a C6 aliphatic spacer to three aliphatic fatty acid (C16) via Tris molecule);
15) CS039: K3ATM3 (trilysine with a short alanine spacer to three aliphatic fatty acid (C16) via Tris molecule);
16) CS015: K3ATP3 (trilysine with a short alanine spacer to three aliphatic fatty acid (C16) via Tris molecule).

CS096, CS102, CS129, CS078, CS051, CS027, CS041, CS042, CS060, CS039 and CS015 are specific examples of transfection promoting agents suitable for the methods and compositions of the invention, the method for synthesizing which is detailed in WO 96/05218, U.S. Pat. No. 5,583,198, U.S. Pat. No. 5,869,606 and U.S. Pat. No. 5,854,224 (see below) and Cameron et al. (1999).

As used in the present invention, the terms "micelle" and "liposome" mean vesicles composed of amphiphilic lipids self-assembled in aqueous solution to form tertiary structures.

Liposomes are unilamellar or multilamellar vesicles of bilayers which have a membrane formed from a lipophilic material and an aqueous interior. The aqueous portion may be organised to contain the composition to be delivered.

Cationic liposomes carry positivel charges on their hydrophilic head-group forming liposomes that interact with the negatively charged nucleic acid molecules to form a complex. The positively charged liposome/nucleic acid complex binds to the negatively charged cell surface and is internalized predominantly through the endosomal pathway. A proportion of the endosomes, will rupture, releasing their contents of liposome/nucleic acid complex into the cell cytoplasm.

Liposomes that are pH-sensitive or negatively charged, entrap nucleic acid rather than complex with it. Since both the nucleic acid and the lipid are similarly charged, repulsion rather than complex formation occurs. Nevertheless, nucleic acid can be entrapped within the aqueous interior of these liposomes.

One major type of liposomal composition includes phospholipids other than naturally derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen and Chonn, 1987; Wu et al., 1993).

A number of liposomes comprising nucleic acids are known in the art. WO 96/40062 discloses methods for encapsulating high molecular weight nucleic acids in liposomes. U.S. Pat. No. 5,264,221 discloses protein-bonded liposomes and asserts that the contents of such liposomes can include an antisense RNA. U.S. Pat. No. 5,665,710 describes certain methods of encapsulating oligodeoxynucleotides in liposomes. WO 97/04787 discloses liposomes comprising antisense oligonucleotides targeted to the raf gene.

Transfection promoting agents useful for the methods and compositions of the present invention include "Tris cationic lipids" which are disclosed in WO 96/05218, U.S. Pat. No.

5,854,224, U.S. Pat. Nos. 5,583,198 and 5,869,606, the contents of which are incorporated by reference. These agents include compounds having a formula selected from the group consisting of:

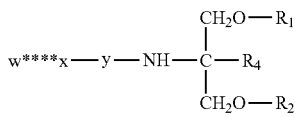
i)

in which:
w is a dsRNA or a nucleic acid encoding a dsRNA
x is a peptide, amino acid, non-amino acid nucleic acid binding group or non-peptide nucleic acid binding group
y is a linker having a chain length equivalent to 1 to 20 carbon atoms or is absent
$R_4$ is H or $CH_2O$—$R_3$; and $R_1$, $R_2$ and $R_3$ are the same or different and are either hydrogen, methyl, ethyl, hydroxyl or an acyl group derived from a fatty acid having a carbon chain of 3 to 24 carbon atoms saturated or unsaturated, with the proviso that at least one of $R_1$, $R_2$ and $R_3$ is an acyl group derived from a fatty acid;

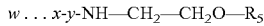
ii)

in which:
w is a dsRNA or a nucleic acid encoding a dsRNA
x is a peptide, amino acid, non-amino acid nucleic acid binding group or non-peptide nucleic acid binding group
y is a linker having a chain length equivalent to 1 to 20 carbon atoms or is absent
$R_5$ is an acyl group derived from a fatty acid having a carbon chain of 3 to 24 carbon atoms saturated or unsaturated;

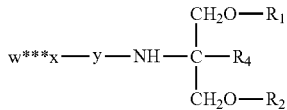
iii)

in which: GP-22,C1
w is a dsRNA or a nucleic acid encoding a dsRNA
x is a peptide, amino acid, non-amino acid nucleic acid binding group or non-peptide nucleic acid binding group
y is a linker having a chain length equivalent to 1 to 20 carbon atoms or is absent
$R_4$ is H or $CH_2O$—$R_3$; and $R_1$, $R_2$ and $R_3$ are the same or different and are either hydrogen, methyl, ethyl, hydroxyl or an acyl group derived from a fatty acid having a carbon chain of 3 to 24 carbon atoms saturated or unsaturated, with the proviso that at least one of $R_1$, $R_2$ and $R_3$ is an acyl group derived from a fatty acid;

iv)

in which:
w is a dsRNA or a nucleic acid encoding a dsRNA
x is a peptide, amino acid, non-amino acid nucleic acid binding group or non-peptide nucleic acid binding group
y is a linker having a chain length equivalent to 1 to 20 carbon atoms or is absent
$R_5$ is an acyl group derived from a fatty acid having a carbon chain of 3 to 24 carbon atoms saturated or unsaturated; and

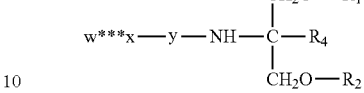
v)

in which:
w is a dsRNA or a nucleic acid encoding a dsRNA
x is a peptide, amino acid, non-amino acid nucleic acid binding group or non-peptide nucleic acid binding group
y is a spacer having a chain length equivalent to 1-30 carbon-carbon single covalent bonds or is absent
$R_4$ is H or halogen or $CH_2O$—$R_3$; and $R_1$, $R_2$ and $R_3$ are the same or different and are either hydrogen, methyl, ethyl, alkyl, alkenyl, hydroxylated alkyl, hydroxylated alkenyl groups or ether containing alkyl, alkenyl, hydroxylated alkyl or hydroxylated alkenyl groups, optionally being an acyl group derived from a fatty acid having a carbon chain length equivalent to 3-24 carbon atoms saturated or unsaturated, with the proviso that at least one of $R_1$, $R_2$ and $R_3$ includes a group having a carbon chain of 3-24 carbon atoms saturated or unsaturated.

Within the meaning of the present invention, the term lipopolyamine denotes any amphiphilic molecule comprising at least one hydrophilic polyamine region and one lipophilic region. The cationically charged polyamine region of the lipopolyamines is capable of combining reversibly with the negatively charged nucleic acid. This interaction strongly compacts the nucleic acid. The lipophilic region makes this ionic interaction less sensitive to the external medium, by covering the nucleolipid particle formed with a lipid layer. Examples of suitable lipopolyamines include those disclosed in U.S. Pat. No. 6,172,048 and U.S. Pat. No. 6,171,612.

Advantageously, the polyamine region of the lipopolyamines used in the context of the invention corresponds to the general formula:

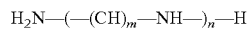

in which m is an integer greater than or equal to 2 and n is an integer greater than or equal to 1, it being possible for m to vary between the different carbon groups included between two amines. Preferably, m is between 2 and 6 inclusive and n is between 1 and 5 inclusive. Still more preferably, the polyamine region is represented by spermine or an analogue of spermine that has retained its properties of binding to nucleic acids.

The lipophilic region can be a saturated or unsaturated hydrocarbon chain, cholesterol, a natural lipid or a synthetic lipid capable of forming lamellar, cubic, or hexagonal phases.

There was some variation in effectiveness of the transfection reagents tested in the arthropod species that were examined. However, considering the present disclosure, it is well within the capacity of the skilled addressee to design routine experiments to test a number of transfection promoting agents to determine which provides the best results for any given arthropod species.

Agriculturally Acceptable Carriers

Agriculturally suitable and/or environmentally acceptable compositions for arthropod control are known in the art. Agricultural compositions for the control of arthropod pests of plants and/or animals are preferably suitable for agricultural use and dispersal in fields. Preferably, compositions for the control of other arthropod pests should be environmentally acceptable.

Agriculturally acceptable carriers are also referred to herein as an "excipient". An excipient can be any material that the animal, plant or environment to be treated can tolerate. Furthermore, the excipient must be such that the composition of the present invention is still capable of causing gene silencing. Examples of such excipients include water, saline, Ringer's solution, dextrose or other sugar solutions, Hank's solution, and other aqueous physiologically balanced salt solutions, phosphate buffer, bicarbonate buffer and Tris buffer. In addition, the composition may include compounds that increase the half-life of a composition. Such compounds are be known to the skilled person in the art.

Compositions of the invention may also comprise agents selected from; conventional pesticides, gustatory stimulants, thickening agents, UV screening agents, optical brighteners, dispersants, flow agents, spreading agents and sticking agents. Preferably, the composition is formulated such that is persist in the environment for a length of time suitable to allow it to be ingested by a target arthropod or contact the target arthropod.

Arthropods

The arthropod can be any organism classified in this taxonomical group. Preferably, the arthropod is selected from the group consisting of: Crustacea, Insecta and Arachnida.

Examples of preferred Insecta include, but are not limited to, members of the orders Coleoptera (e.g. *Anobium, Ceutorhynchus, Rhynchophorus, Cospopolites, Lissorhoptrus, Meligethes, Hypothenemus, Hylesinus, Acalymma, Lema, Psylliodes, Leptinotarsa, Gonocephalum, Agriotes, Dermolepida, Heteronychus, Phaedon, Tribolium, Sitophilus, Diabrotica, Anthonomus* or *Anthrenus* spp.), Lepidoptera (e.g. *Ephestia, Mamestra, Earias, Pectinophora, Ostrinia, Trichoplusia, Pieris, Laphygma, Agrotis, Amathes, Wiseana, Tryporyza, Diatraea, Sporganothis, Cydia, Archips, Plutella, Chilo, Heliothis, Helicoverpa* (especially *Helicoverpa armigera*), *Spodoptera* or *Tineola* ssp.), Diptera (e.g. *Musca, Aedes, Anopheles, Culex, Glossina, Simulium, Stomoxys, Haematobia, Tabanus, Hydrotaea, Lucilia, Chrysomia, Callitroga, Dermatobia, Gasterophilus, Hypoderma, Hylemyia, Atherigona, Chlorops, Phytomyza, Ceratitis, Liriomyza,* and *Melophagus* spp.), Phthiraptera, Hemiptera (e.g. *Aphis, Bemisia, Phorodon, Aeneoplamia, Empoasca, Parkinsiella, Pyrilla, Aonidiella, Coccus, Pseudococcus, Helopeltis, Lygus, Dysdercus, Oxycarenus, Nezara, Aleurodes, Triatoma, Rhodnius, Psylla, Myzus, Megoura, Phylloxera, Adelyes, Niloparvata, Nephrotettix* or *Cimex* spp.), Orthoptera (e.g. *Locusta, Gryllus, Schistocerca* or *Acheta* spp.), Dictyoptera (e.g. *Blattella, Periplaneta* or *Blatta* spp.), Hymenoptera (e.g. *Athalia, Cephus, Atta, Lasius, Solenopsis* or *Monomorium* spp.), Isoptera (e.g. *Odontotermes* and *Reticulitermes* spp.), Siphonaptera (e.g. *Ctenocephalides* or *Pulex* spp.), Thysanura (e.g. *Lepisma* spp.), Dermaptera (e.g. *Forficula* spp.) and Psocoptera (e.g. *Peripsocus* spp.) and Thysanoptera (e.g. *Thrips tabaci*). In one embodiment, the Arthropod is not a *Drosophila* sp.

Examples of preferred Arachnida include, but are not limited to, ticks, e.g. members of the genera *Boophilus, Ornithodorus, Rhipicephalus, Amblyomma, Hyalomma, Ixodes, Haemaphysalis, Dermocentor* and *Anocentor*, and mites and manges such as *Acarus, Tetranychus, Psoroptes, Notoednes, Sarcoptes, Psorergates, Chorioptes, Demodex, Panonychus, Bryobia* and *Eriophyes* spp.

Examples of preferred Crustaceans include, but are not limited to, crayfish, prawns, shrimps, lobsters and crabs.

Recombinant Vectors

Polynucleotides encoding dsRNA useful for the methods and/or compositions of the present invention can be inserted into a recombinant vector. The vector can be either RNA or DNA, either prokaryotic or eukaryotic, and typically is a virus or a plasmid.

One type of recombinant vector comprises a polynucleotide encoding a dsRNA operatively linked to an expression vector. Alternatively, the two strands of the dsRNA are encoded by separate open reading frames. The phrase operatively linked refers to insertion of a polynucleotide molecule into an expression vector in a manner such that the molecule is able to be expressed when transformed into a host cell. As used herein, an expression vector is a DNA or RNA vector that is capable of transforming a host cell and of effecting expression of a specified polynucleotide molecule(s). Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, endoparasite, arthropod, other animal, and plant cells. Preferred expression vectors of the present invention can direct gene expression in arthropod cells.

In particular, expression vectors of the present invention contain regulatory sequences such as transcription control sequences, origins of replication, and other regulatory sequences that are compatible with the recombinant cell and that control the expression of the polynucleotide encoding a dsRNA or a strand thereof. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in arthropod cells. Additional suitable transcription control sequences include tissue-specific promoters and enhancers.

A particularly preferred expression vector is a baculovirus. By "baculovirus" it is meant any virus of the family Baculoviridae, such as a nuclear polyhedrosis virus (NPV). Baculoviruses are a large group of evolutionarily related viruses, which infect only arthropods; indeed, some baculoviruses only infect insects that are pests of commercially important agricultural and forestry crops, while others are known that specifically infect other insect pests. Because baculoviruses infect only arthropods, they pose little or no risk to humans, plants, or the environment.

Of the suitable DNA viruses, in addition to the Baculoviridae are the entomopox viruses (EPV), such as *Melolontha melonotha* EPV, *Amsacta moorei* EPV, *Locusta migratoria* EPV, *Melanoplus sanguinipes* EPV, *Schistocerca gregatia* EPV, *Aedes aogypti* EPV, and *Chironomus ludidus* EPV. Other suitable DNA viruses are granulosis viruses (GV). Suitable RNA viruses include togaviruses, flaviviruses, picornaviruses, cytoplasmic polyhedrosis viruses (CPV), and the like. The subfamily of double stranded DNA viruses Eubaculovirinae includes two genera, NPVs and GVs, which are particularly useful for biological control because they produce occlusion bodies in their life cycle. Examples of GVs include *Cydia pomonella* GV (coddling moth GV), *Pieris brassicae* GV, *Trichoplusia ni* GV, *Artogeia rapae* GV, and *Plodia interpunctella* GV (Indian meal moth).

Suitable baculoviruses for practicing this invention may be occluded or non-occluded. The nuclear polyhedrosis viruses ("NPV") are one baculovirus sub-group, which are "occluded." That is, a characteristic feature of the NPV group is that many virions are embedded in a crystalline protein matrix referred to as an "occlusion body." Examples of NPVs include *Lymantria dispar* NPV (gypsy moth NPV), *Autographa californica* MNPV, *Anagrapha falcifera* NPV (celery looper NPV), *Spodoptera litturalis* NPV, *Spodoptera frugiperda* NPV, *Heliothis armigera* NPV, *Mamestra brassicae* NPV, *Choristoneura fumiferana* NPV, *Trichoplusia ni* NPV, *Helicoverpa zea* NPV, and *Rachiplusia ou* NPV. For field use occluded viruses often are preferable due to their greater stability since the viral polyhedrin coat provides protection for the enclosed infectious nucleocapsids.

Among illustrative, useful baculoviruses in practicing this invention are those isolated from *Anagrapha falcifera, Anticarsia gemmatalis, Buzura suppressuria, Cydia pomonella, Helicoverpa zea, Heliothis armigera, Manestia brassicae, Plutella xylostella, Spodoptera exigua, Spodoptera littoralis,* and is *Spodoptera litura*. A particularly useful "NPV" baculovirus for practicing this invention is AcNPV, which is a nuclear polyhedrosis virus from *Autographa californica*. *Autographa californica* is of particular interest because various major pest species within the genera *Spodoptera, Trichoplusia,* and *Heliothis* are susceptible to this virus.

Transgenic Plants

The term "plant" refers to whole plants, plant organs (e.g. leaves, stems roots, etc), seeds, plant cells and the like. Plants contemplated for use in the practice of the present invention include both monocotyledonous and dicotyledonous plants. Exemplary dicotyledonous plants include cotton, oilseeds and other brassicas, tomato, tobacco, potato, bean, and soybean. Exemplary monocotyledonous plants include wheat, maize, barley, rice, and sorghum. The choice of the plantspecies is determined by the intended use of the plant or parts thereof and the amenability of the plant species to transformation.

Transgenic plants, as defined in the context of the present invention include plants (as well as parts and cells of said plants) and their progeny which have been genetically modified using recombinant DNA techniques to produce at least one dsRNA useful for the methods of the present invention in the desired plant or plant organ.

A polynucleotide encoding a dsRNA, or two different polynucleotides encoding individual strands of a dsRNA, may be expressed constitutively in the transgenic plants during all stages of development. Depending on the use of the plant or plant organs, the dsRNA may be produced in a stage-specific manner. Furthermore, depending on the use, the polynucleotides may be expressed tissue-specifically or induced under specific environmental condition such as for example, wounding by an arthropod pest.

Regulatory sequences which are known or are found to cause expression of a polynucleotide(s) encoding a dsRNA of interest in plants may be used in the present invention. The choice of the regulatory sequences used depends on the target crop and/or target organ of interest and the desired mode of expression (e.g. constitutive induced or tissue specific). Such regulatory sequences may be obtained from plants or plant viruses, or may be chemically synthesized. Such regulatory sequences are well known to those skilled in the art.

Other regulatory sequences such as terminator sequences and polyadenylation signals include any such sequence functioning as such in plants, the choice of which are known to the skilled addressee. An example of such sequences is the 3' flanking region of the nopaline synthase (nos) gene of *Agrobacterium tumefaciens*.

Several techniques are available for the introduction of an expression construct containing a polynucleotide(s) encoding a dsRNA of interest into the target plants. Such techniques include but are not limited to transformation of protoplasts using the calcium/polyethylene glycol method, electroporation and microinjection or (coated) particle bombardment. In addition to these so-called direct DNA transformation methods, transformation systems involving vectors are widely available, such as viral and bacterial vectors (e.g. from the genus *Agrobacterium*). After selection and/or screening, the protoplasts, cells or plant parts that have been transformed can be regenerated into whole plants, using methods known in the art. The choice of the transformation and/or regeneration techniques is not critical for this invention.

EXAMPLES

Methods

GUS RNA In Vitro Transcription Plasmids

Standard gene cloning methods (Sambrook et al., 1989) were used to make the gene constructs. The GUS gene encoding the bacterial enzyme β-glucuronidase was amplified by PCR from the pBacPAK8-GUS plasmid (Clonetech) using the primers EcoGusF (GAATTCATGGTCCGTCCTGTA-GAAACC) (SEQ ID NO: 1) and EcoGusR (GAATTC-CCCCACCGAGGCTGTAGC) (SEQ ID NO: 2). The 1.87 kb PCR product was subcloned into the plasmid pGEM3Zf(+) into the EcoR I site using the EcoR I linkers on the primers, creating two plasmids: pGEM3Z-GUS[s](sense orientation of GUS gene, relative to the T7 promoter); and pGEM3Z-GUS[a/s](antisense orientation of GUS gene, relative to the T7 promoter). Both plasmids were digested with the restriction endonuclease EcoRV, followed by religation of the plasmid, to remove 213 bp of the GUS ORF. This ensured that no functional GUS enzyme would be produced if the sense GUS RNA was translated. The resultant plasmids, named pGEM3Z-ΔGUS[s] and pGEM3Z-ΔGUS[a/s], were used for in vitro transcription of sense and antisense GUS RNAs.

GUS RNA In Vivo Expression Constructs

In vivo expression of sense, antisense, and inverted repeat RNA in *D. melanogaster* embryos was achieved by preparing three plasmids that expressed RNA under the control of the *D. melanogaster* heat shock promoter hsp70. A 1 kb fragment containing the hsp70 promoter, a small multiple cloning site, and the heat shock polyadenylation signal was amplified using PCR from the plasmid pCaSpeR-hs (Thummel et al., 1988) using the primers hsp70F (GAATTCTAGAATC-CCAAAACAAACTGG) (SEQ ID NO: 3) and hst70R (GGATCCTGACCGTCCATCGCAATAAAATGAGCC) (SEQ ID NO: 4).

The 1 kb PCR product was cloned into pGEM-T-Easy, resulting in the plasmid pGEM-Dmhsp70. The GUS gene was excised from the plasmid pGEM3Z-GUS[s] using the restriction endonuclease EcoRI, and ligated into the pGEM-Dmhsp70 plasmid, previously linearized with EcoRI. This ligation resulted in two plasmids, phspGUS[s], with the GUS gene in the sense orientation with respect to the promoter, and phspGUS[a/s], with the GUS gene in the antisense orientation. A third plasmid, pHSP70GUS[i/r], was prepared that expressed an inverted repeat dsRNA specific to the GUS open reading frame (ORF), by ligating a 558 bp DNA fragment, representing the 5' end of the GUS gene, to the 3' end of the GUS ORF. The resulting coding sequence, when transcribed, could produce a transcript with complementary sequences at the 5' and 3' ends, which could fold back upon itself to form a hairpin dsRNA, with double-stranded sequence for 558 bases.

H. armigera vATPase In Vitro Transcription Plasmids

A 386 bp segment of a putative vATPase gene was amplified from H. armigera genomic DNA using the two primers HaATP1f (CCGAAAATCCAATCTACGGACCC) (SEQ ID NO: 5) and HaATP1r (CGACGAATAACCTGGGCTGTTGC) (SEQ ID NO: 6). The primers were based on DNA sequence of a putative vATPase gene identified from a H. armigera EST clone that showed 97% sequence identity to the vATPase gene of Heliothis virescens (GenBank accession #L16884). The 386 bp product was amplified using a Perkin Elmer 2400 Thermocycler using the following PCR conditions: 1 cycle of 95° C. for 5 min, 25 cycles of 95° C.×30 sec, 55° C.×30 sec, 72° C.×30 sec, and 1 cycle of 72° C.×10 min, 25° C.×5 min. The PCR product was ligated into the pGem-T-Easy cloning vector (Promega) in both orientations with respect to the T7 promoter, producing the plasmids pGEM-HaATPase1[s] and pGEMHaATPase1[a/s], which were used to produce in vitro transcribed sense and antisense vATPase RNAs.

Drosophila Transformation

The GUS gene encoding the bacterial enzyme β-glucuronidase, was inserted into the P-element transformation vector pCaSpeR-act, which placed the GUS gene under the control of the act5c promoter. The GUS gene was then introduced into the Drosophila germline by P-element transformation (Spradling and Rubin, 1982). Transformants were back-crossed to chromosomal balancer strains to identify into which chromosome the transgene had inserted. Southern analyses of DNA from G2 flies were preformed to determine the copy number of the transgene in the GUS transgenic stock.

Preparation of Double-Stranded RNA by In Vitro Transcription

The plasmids pGEM3Z-ΔGUS[s] and -ΔGUS [a/s] were linearized using Bam HI. Sense and antisense RNA was prepared using T7 RNA polymerase using Promega's RiboMAX Large Scale RNA Production System, according to the manufacturer's instructions. To produce dsRNA, sense and antisense RNAs were mixed in equimolar quantities and annealed for 10 minutes at 37° C. The RNA was extracted with phenol/chloroform and then chloroform, precipitated with ethanol, and resuspended in 10 mM Tris-HCl, pH 9. Formation of dsRNA was confirmed by resolving the annealed and non-annealed RNAs on a 1.0% agarose gel in TBE (90 mM Tris-borate, 2 mM EDTA, pH 8.0).

To produce vATPase dsRNA, the plasmids pGEMHaATPase1[s] and pGEMHaATPase1[a/s] were linearized with Bam HI and sense, antisense, and double-stranded RNAs were produced as described above.

Embryo Injections

Preblastoderm D. melanogaster embryos were microinjected with DNA or RNA according to the method of Spradling and Rubin (1982) and H. armigera embryos were microinjected as previously described (Pinkerton et al., 1996). The embryos were injected with sense, antisense, and dsRNAs dissolved in injection buffer (5 mM KCl, 0.1 mM PO$_4$, pH 6.8) at a concentration of 100 ng/ul. Approximately 50 pg of RNA were injected in each embryo. Negative control embryos were mock-injected with injection buffer alone. Embryos injected with DNA were injected with approximately 250 pg of plasmid DNA. The embryos were permitted to fully develop for 16 h, and were either snap frozen for use in subsequent GUS assays or were permitted to hatch and surviving larvae were transferred to vials containing culture medium. Individual larvae and adult insects were collected and snap frozen at −80° C.

Oral dsRNA Delivery

Newly hatched 1$^{st}$ instar larvae (Drosophila melanogaster or Helicoverpa armigera) were transferred to 96-well plates in groups of 10-25, and washed in phosphate buffered saline (PBS). Sense, antisense, and annealed dsRNAs (0.05-2 ug) were mixed with 1 ul of transfection promoting agent, 0.5 mM spermidine or protamine sulphate (0.5 mg/mg DNA), in a volume of 20 ul of PBS or buffered sucrose (20% sucrose, 10 mM Tris, pH 7.5). After 30 min, red food dye was added to the transfection promoting agent-RNA mixture and the mixture was added to the neonate larvae. The larvae remained immersed in the mixtures for 1 h, and larvae were then transferred to rearing medium. Approximately 90% of individuals treated in this manner contained red food dye in their guts, indicating that most had ingested the mixture.

Rearing Conditions

D. melanogaster were raised at 25° C. on standard yeast-agar Drosophila culture media (Roberts and Standen, 1998). H. armigera were raised as previously described (Duve et al., 1997).

GUS Assays

Insects were homogenised in homogenisation buffer (50 mM NaHPO$_4$, pH 7.0, 10 mM O-mercaptoethanol, 10 mM EDTA, 0.1% sodium lauryl sarcosine, 0.1% Triton X-100), and GUS enzyme activity was measured using 4-methylumbelliferyl β-D-glucuronic acid as a substrate in fluorometric assays as described (Gallagher, 1992). Protein assays were performed using the Bradford assay (Bradford, 1976). Dissected insects were stained for GUS activity using 5-bromo-4-chloro-3-indolyl β-D-glucuronic acid (X-GlcU) as described (Naleway, 1992).

Results

Characterisation of the GUS Transgenic Strain

Standard genetic and Southern analyses confirmed that the GUS transgenic stock of D. melanogaster contained a single insertion of the act5c-GUS construct, located on chromosome III (results not shown). The GUS gene was constitutively expressed throughout the body, with extensive GUS activity observed in the fat body and gonads of both males and females (data not shown). Fluorometric GUS enzyme assays confirmed that all developmental stages of the GUS transgenics had at least 18 times more GUS activity than their non-transformed counterparts (Table 1).

Silencing of the GUS Gene in Drosophila Embryos Using In Vitro Transcribed and Annealed Double Stranded RNA Following injection of RNA into preblastoderm embryos, embryos were permitted to develop for 16 h, just prior to hatching, before they were assayed for GUS activity. Embryos were pooled in groups of 25, whereas larvae and adults were assayed individually for GUS activity. While it was not possible to determine which individual embryos were most affected by the RNA injections, it was clear that both sense and antisense had no or little affect on GUS activity, whereas those embryos injected with dsRNA showed significant reductions in GUS activity (Table 2). Northern analyses of RNA from mock-injected and dsRNA-injected embryos confirmed that the reduction of GUS activity correlated with reduction of GUS transcripts in the dsRNA-injected embryos (results not shown). Interestingly, the silencing of the GUS gene expression persisted throughout development, as both larvae and adults that had been treated with dsRNA as embryos still showed substantial reductions in GUS activity.

These results confirmed that GUS gene expression could be effectively reduced by direct delivery of in vitro-prepared dsRNA into the embryos.

TABLE 1

GUS activity in non-transgenic and transgenic D. melanogaster

| Developmental stage | GUS activity (pmol MU/min/individual) | | Fold increase in GUS activity in transgenics |
|---|---|---|---|
| | Non-transgenic | Transgenic | |
| embryo | 74 ± 20 | 1980 ± 152 | 27 |
| $3^{rd}$ instar larva | 417 ± 34 | 7390 ± 780 | 18 |
| adult | 574 ± 55 | 12620 ± 827 | 22 |

TABLE 2

Reduction of GUS activity following embryonic injection of RNA to D. melanogaster GUS strain embryos. Values represent the percentage decrease (±standard error) of GUS activity relative to mock-injected embryos.

| | Reduction in GUS activity following delivery of RNA (%) | | |
|---|---|---|---|
| | Embryos[1] | Larvae[2] | Adults[2] |
| Sense RNA | 2 ± 1 | 3 ± 2 | 5 ± 3 |
| Antisense RNA | 9 ± 4 | 7 ± 5 | 15 ± 8 |
| ds RNA | 65 ± 14 | 41 ± 7 | 32 ± 5 |

[1]Values represent results from 3 separate replicates of 25 embryos each.
[2]Values represent results from 3 separate replicates of 10 individuals each.

Silencing of the GUS Gene in *Drosophila* Embryos Using In Vivo-Produced dsRNA

GUS strain embryos were injected with the plasmids phspGUS[s], phspGUS[a/s], and phspGUS[i/r], and then heat shocked 6 h post injection. The embryos were collected just prior to hatching (16 h development), and were assayed for GUS activity. The embryos injected with phspGUS[s] showed no difference in GUS activity, whereas embryos injected with phspGUS[a/s] showed a 12% decrease in GUS activity relative to mock-injected controls (Table 3). Embryos injected with the inverted repeat RNA expression construct, phspGUS[i/r], showed substantial (90%) reduction of GUS activity. Adults that developed from embryos injected with the phspGUS[i/r] plasmid showed persistence of the gene silencing phenotype, having a 55% reduction in GUS activity relative to mock-injected controls. Adults derived from injections of plasmids that expressed sense or antisense RNA showed no persistence of the gene silencing.

TABLE 3

Reduction of GUS activity following embryonic injection of RNA-expression plasmids to D. melanogaster GUS strain embryos. Values represent the percentage decrease (±standard error) of GUS activity relative to mock-injected embryos.

| | Reduction in GUS activity (%) | |
|---|---|---|
| | Embryos | Adults |
| phspGUS[s] | 1 ± 1 | 1 ± 2 |
| phspGUS[a/s] | 12 ± 2 | 2 ± 1 |
| hspGUS[i/r] | 90 ± 8 | 55 ± 6 |

PCR analysis of different developmental stages showed that the injected plasmid could not be detected beyond first instar larvae (FIG. 1), suggesting that the injected DNA was quickly degraded once the insects moulted into $2^{nd}$ instar larvae. The persistence of the gene silencing throughout development was therefore most likely due to the persistence of the dsRNA, and not due to sustained expression of dsRNA from the injected plasmid.

Silencing of the GUS Gene in *Drosophila* Following Soaking of Larvae in dsRNA

Figure 2:
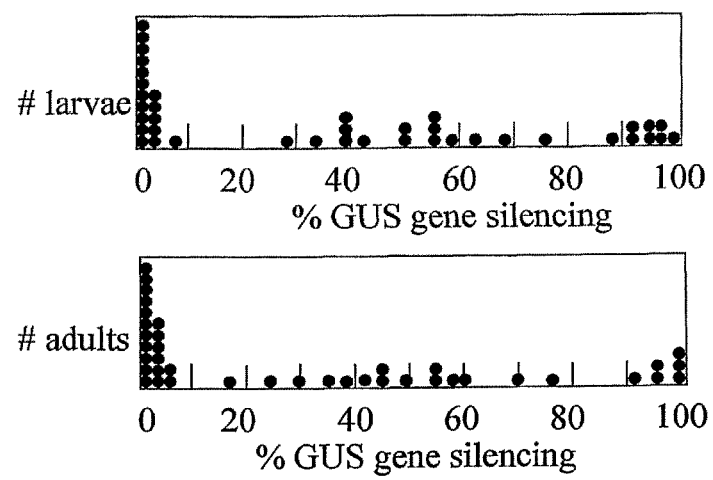
FIG. 2. Gene silencing in *D. melanogaster* larvae and adults after feeding neonates dsRNA. Neonate larvae were soaked in a composition comprising transfection promoting agent and GUS dsRNA, and individuals were assayed either as $2^{nd}$ instar larvae (top panel) or as adults (bottom panel). A total of 40 individuals were assayed for each group. Each dot represents one individual's level of GUS gene silencing, relative to non-treated controls FIG. 3. Reduced GUS activity following soaking of neonate larvae in a composition comprising transfection promoting agent and different concentrations of dsRNA. Each dot represents one individual adult fly's GUS activity, as a percentage of non-treated GUS controls. A total of 20 flies were assayed for each concentration of dsRNA.

*Drosophila* larvae fed naked GUS dsRNA showed no changes in GUS gene expression (results not shown). Similarly, no change in GUS activity in $2^{nd}$ instar larvae or adults was observed when neonate larvae were immersed in a DMRIE-C mixture containing GUS sense or antisense RNA (results not shown). In contrast, 15% of neonates soaked in transfection promoting agent containing GUS dsRNA developed into adult flies that showed >90% reduction of GUS activity (FIG. 2). Another 35% of the surviving flies showed an intermediate (20-80%) reduction of GUS expression. Similarly, $2^{nd}$ instar larvae derived from neonates soaked in dsRNA showed a similar result, with 20% of larvae having >90% reduction of GUS activity, and another 40% of the larvae showing a reduction of GUS activity between 20% and 80% of normal GUS activity levels. These results indicate that in vitro transcribed and annealed dsRNA can be fed to neonates and cause extensive, body-wide gene silencing of the target gene. This method of dsRNA delivery seems relatively benign, as no larvae were observed to die or suffer from the transfection promoting agent treatment. Gene silencing appears to be gene specific, as the insects showing reduced GUS activity appeared healthy and showed no other observable phenotype.

As the larvae were soaking in the mixture, it is possible that entry of dsRNA may have occurred either by ingestion, perfusion into the trachea, or by absorption through the cuticle. However, a small percentage (10%) of surviving larvae were observed not to have any food colouring in their guts. These individuals showed no reduction of GUS activity, which suggested that the primary route of entry for the dsRNA is via the alimentary canal (results not shown).

Figure 3:
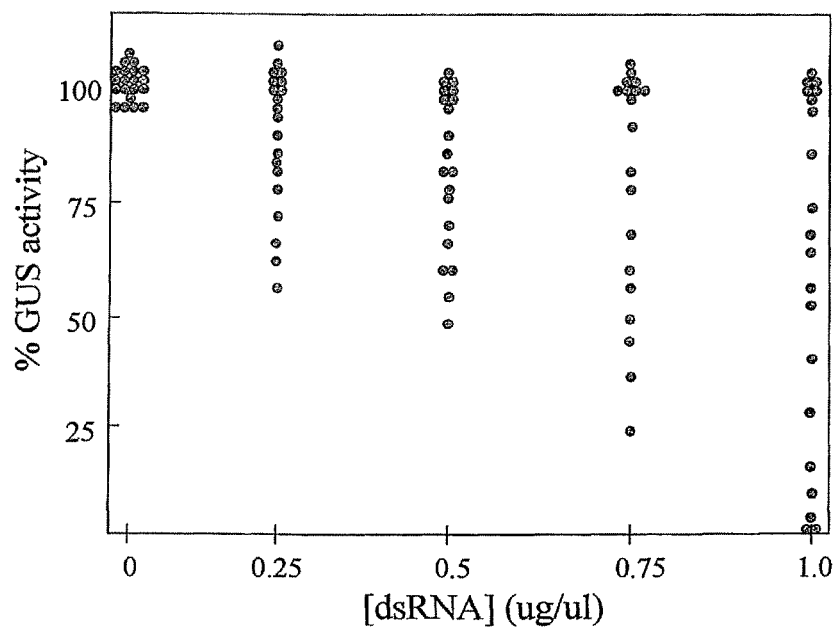

The concentration of dsRNA fed to the larvae correlated directly with the number of individuals that exhibited strong suppression of GUS activity. The lowest concentration (0.25 ug/ul) of dsRNA tested, using DMRIE-C, produced 4/20 flies that displayed a reduction of GUS activity greater than 25% (FIG. 3). In contrast, the highest concentration of dsRNA tested (1.0 ug/ul) produced 12/20 flies with a reduction of GUS activity greater than 25%. At this highest dose, the greatest number of flies (5120) showed a reduction of GUS activity of greater than 80%. While these sample sizes are small (20 individuals/treatment), they indicate that the extent of gene silencing may be dsRNA dose-dependent.

Figure 4:
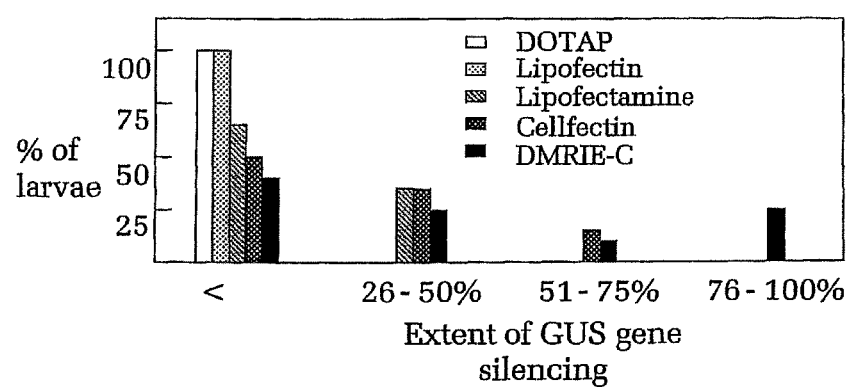
FIG. 4. Effectiveness of different transfection promoting agents on the oral delivery of dsRNA to neonate *D. melanogaster* larvae. A total of 20 larvae were soaked in different transfection promoting agents containing 1 ug/ul dsRNA, and the GUS activity was assessed in $2^{nd}$ instar larvae.

Lipofectamine, Cellfectin, and DMRIE-C (Life Technologies), each produced individuals with a measurable level of reduced GUS activity (FIG. 4). DMRIE-C provided the greatest number of individuals with extensive gene silencing, with 25% of the larvae having greater than 75% of the GUS activity eliminated. Two individuals out of 20 showed 100% gene silencing using this transfection promoting agent. Transfections with Lipofectamine and Cellfectin resulted in 26-50% silencing of the GUS gene in 35% of the larvae tested, which indicates that these transfection promoting agents could also serve to deliver dsRNA to *Drosophila* via ingestion.

Given that most (approximately 70%, results not shown) of the GUS gene expression is found in the fat body and gonads, the silencing signal had obviously passed beyond the gut tissues and spread throughout the body. This gene silencing spreading phenomenon is not unlike that seen in *C. elegans* nematodes fed dsRNA. However, it is surprising to observe gene silencing in the insect following this mode of delivery of dsRNA, as the gut of *Drosophila* is physically and physiologically more complex than that of *C. elegans*. Most notably, *Drosophila* produces a peritrophic membrane throughout the length of the midgut, which theoretically could potentially reduce or prevent transmission of dsRNA to the midgut cells.

Figure 5:
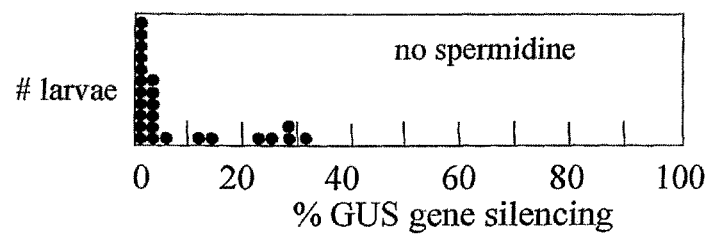
FIG. 5. Gene silencing in *D. melanogaster* larvae after feeding neonates dsRNA, without the presence of spermidine in the RNA mixture. Neonate larvae were soaked in a composition comprising transfection promoting agent and GUS dsRNA, and individuals were assayed as $2^{nd}$ instar larvae. A total of individuals were assayed, with each dot representing one individual's level of GUS gene silencing, relative to non-treated controls.

Addition of a nucleic acid condensing agent (spermidine or protamine sulfate) to the RNA mixture was found to enhance the efficiency of RNAi in *Drosophila*. Without adding spermidine, only 20% of treated larvae displayed a reduction of GUS activity greater than 20%, and only a maximum of 32% GUS silencing was observed (FIG. 5). Not only did the percentage of individuals with significant levels of GUS gene silencing increase by using spermidine, but the maximum level of GUS gene silencing increased to 100% in some individuals (see FIG. 2). A similar enhancement of RNAi was observed if protamine sulphate was used instead of spermidine (results not shown).

The efficiency of RNAi in *Drosophila* was found to improve slightly when PBS was replaced with buffered sucrose during the mixing of the RNA with the transfection promoting agents (Table 4). Although it has not been examined further, it is anticipated that replacement of PBS with sucrose will improve efficiency of the packaging of the RNA in many of the transfection promoting agents under consideration.

A selection of transfection promoting agents was kindly provided by Trevor Lockett and colleagues (CSIRO Molecular Science). These transfection promoting agents are thoroughly described in the patent "Delivery of Nucleic Acids" (PCT/AU95100505, U.S. Pat. No. 5,906,922). A comparison of 11 of these CSIRO reagents with the 5 commercially available reagents was conducted, and many of the CSIRO liposomes were more effective at producing an RNAi effect in *Drosophila* (Table 5). In particular, liposomes CS096, CS102, and CS129 performed better than the best-performing commercially available liposome, DMRIE-C. All of the CSIRO liposomes tested produced a greater number of individuals affected by RNAi than the poorest commercially available liposome, DOTAP. These results confirm that optimised delivery of dsRNA to insects can be achieved by selecting appropriate transfection promoting agents.

TABLE 4

Percentage of $2^{nd}$ instar larvae showing greater than a 25% reduction of GUS gene activity following soaking in transfection promoting agents that were mixed with RNA in either PBS or buffered sucrose solutions. Values represent the mean and standard deviation from two replicates of 25 insects.

| Transfection Promoting Agent | PBS | Buffered Sucrose |
| --- | --- | --- |
| DMRIE-C | 60 ± 7 | 72 ± 10 |
| Lipofectamine | 35 ± 6 | 49 ± 8 |
| DOTAP | 0 ± 0 | 5 ± 3 |

Silencing of an endogenous gene in *H. armigera*

Neonate *H. armigera* were soaked in a composition containing transfection promoting agent and dsRNA specific to a putative vacuolar ATPase gene. Several vATPase genes are present in Lepidoptera, some of which are known to encode subunits of proton pumps in the midgut cells. These proton pumps are responsible for establishing and maintaining the high pH (approximately pH 10) environment of the lepidopteran midgut.

While all *Drosophila* larvae survived the soaking treatment, only 64% of *H. armigera* larvae were alive 24 h after exposure to transfection promoting agent containing no RNA (Table 6). A similar percentage of caterpillars (62%) survived a treatment containing transfection promoting agent mixed with GUS dsRNA. Only 40% of larvae soaked in transfection promoting agent mixed with vATPase dsRNA survived the first 24 h. In addition to a slightly reduced survival after the first 24 hours, delayed development was also observed for larvae exposed to vATPase dsRNA.

Of those larvae surviving beyond 24 h, 85% of the control larvae reached pupation by day 10. In contrast, only 40% of surviving larvae treated with vATPase dsRNA pupated by day 10. The overall mortality for larvae treated with vATPase dsRNA, relative to those treated with transfection promoting agent alone was 52%. Larvae treated with GUS dsRNA were not significantly affected, as 82% had pupated by day 10. Oral delivery of vATPase dsRNA therefore resulted in both reduced survival and delayed development in *H. armigera* larvae.

TABLE 5

Ordered ranking of CSIRO transfection promoting agents and commercially available transfection promoting agents in their ability to induce RNAi of the GUS transgene in *Drosophila*. The percentage of $2^{nd}$ instar larvae having greater than a 25% reduction in GUS activity was determined after neonate larvae were soaked in the transfection promoting agent containing GUS dsRNA in buffered sucrose. Values represent the mean and standard deviation from two experiments with 15 insects each.

| Ranking | Transfection Promoting Agent | % $2^{nd}$ instar larvae with >25% GUS RNAi |
| --- | --- | --- |
| 1 | CS096 | 70 ± 5 |
| 2 | CS102 | 63 ± 14 |
| 2 | CS129 | 63 ± 5 |
| 3 | DMRIE-C | 56 ± 14 |
| 4 | CS078 | 46 ± 9 |
| 5 | CS051 | 43 ± 14 |
| 5 | CS027 | 43 ± 5 |
| 6 | CS041 | 40 ± 9 |
| 7 | Lipofectamine | 36 ± 5 |
| 8 | CS042 | 23 ± 5 |
| 9 | Cellfectin | 20 ± 9 |
| 9 | CS060 | 20 ± 9 |
| 10 | Lipofectin | 16 ± 5 |
| 11 | CS039 | 10 ± 5 |
| 11 | CS015 | 10 ± 5 |
| 12 | DOTAP | 3 ± 5 |

*Complete names of the transfection promoting agents are provided in the "Transfection Promoting Agent" section of the Detailed Description. Lipofectin, Lipofectamine, Cellfectin, and DMRIE-C were obtained from Life Technologies, whereas DOTAP was obtained from Boehringer Mannheim.

Little is known about the expression of the particular vATPase gene that was targeted, other than that it is expressed in gut tissues (as it was isolated from a gut-specific EST library). It is not presently known if the targeted vATPase gene is also expressed elsewhere in the body, nor if the extent of gene silencing was sufficient to reduce the majority of vATPase activity. Nevertheless, the GUS dsRNA produced no deleterious effect on the caterpillars, which indicates that the vATPase dsRNA-mediated gene silencing was sufficiently effective to cause a significant level of mortality and morbidity.

Unlike *D. melanogaster*, the use of Lipofectamine provided the best RNAi (Table 7). As with *Drosophila*, treatments of RNA alone or RNA with spermidine failed to result in observable RNAi.

TABLE 6

Effects of soaking H. armigera larvae in transfection promoting agent containing dsRNA. The results represent the mean and standard errors for three separate experiments using 20 larvae for each treatment.

|  | % surviving larvae at 24 h[a] | % pupated by day 10[b] | % survival to adulthood[c] |
|---|---|---|---|
| Transfection Promoting Agent alone | 64 ± 5 | 85 ± 5 | 100 |
| Transfection Promoting Agent + GUS dsRNA | 60 ± 6 | 82 ± 6 | 91 |
| Transfection Promoting Agent + vATPase dsRNA | 40 ± 12 | 40 ± 5 | 52 |

[a]based on three experiments using 20 insects each
[b]percentage based on those insects surviving past 24 h post treatment
[c]percentage survival relative to the transfection promoting agent treated controls.

Feeding RNA Extracts from Insects that Produce dsRNA

RNA was extracted from a group of 100 flies that had been injected as embryos with the phspGUS[i/r] plasmid. The injected embryos had been subjected to a single heat shock to produce GUS dsRNA during mid embryogenesis. As no plasmid DNA could be detected in developmental stages beyond $1^{st}$ instars, it is not expected that further RNA would be transcribed from this template DNA. The extracted RNA was injected into embryos at a concentration of 1 ug/ul and the embryos were later assayed for GUS activity. GUS activity was reduced by 40% in these embryos, which indicates that the dsRNA is both extractable and still capable of promoting gene silencing when transferred back into naïve insects. RNAs obtained from flies previously injected with either the phspGUS[s] plasmid (sense RNA) or phspGUS[a/s] plasmid (antisense RNA) were also injected into embryos, and these embryos showed no change in GUS activity (results not shown).

TABLE 7

Comparison of transfection promoting agent efficiencies at producing RNAi-induced delayed development in H. armigera. Values represent the percentage of larvae that survived the first 12 h post-treatment that reached pupation by day 10. Six replicates of 10 larvae were tested for each of the conditions.

| RNA mixture | % pupation by day 10 |
|---|---|
| Buffer only | 87 ± 5 |
| RNA + buffer | 84 ± 4 |
| RNA + buffer + spermidine | 82 ± 6 |
| RNA + buffer + spermidine + DOTAP | 73 ± 7 |
| RNA + buffer + spermidine + Lipofectin | 69 ± 10 |
| RNA + buffer + spermidine + Lipofectamine | 48 ± 16 |
| RNA + buffer + spermidine + Cellfectin | 54 ± 9 |
| RNA + buffer + spermidine + DMRIE-C | 53 ± 14 |
| RNA + buffer (no spermidine) + Lipofectamine | 58 ± 8 |

Figure 6:
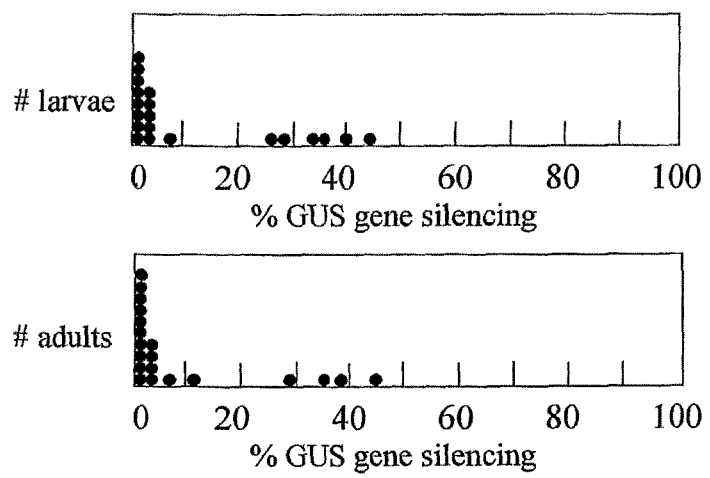
FIG. 6. GUS gene silencing in *D. melanogaster* fed RNA extracts derived from *D. melanogaster* adults that had been injected with the dsRNA expression plasmid phspGUS[i/r] as embryos. The top panel illustrates the range of gene silencing in $3^{rd}$ instar larvae previously fed the extracted RNA, and the bottom panel shows the range of gene silencing observed in adult flies. Each dot represents a single individual insect. A total of 20 individuals were assayed for each group.

The RNA extracted from flies previously injected with the phspGUS[i/r] plasmid was then mixed with DMRIE-C and fed to neonate larvae. Developed larvae and adults were assayed for GUS activity, and 30% of the $3^{rd}$ instar larvae and 20% of the adults showed between 25 and 50% reduction in GUS activity (FIG. 6). These results indicate that dsRNA can be fed to neonates not only as in vitro transcribed and annealed full length inverted repeat dsRNA, but also as dsRNA that has been processed within the insect. Although the proportion of dsRNA relative to the total RNA extracted was not determined, the quantity of dsRNA extracted from the insects was obviously sufficient to promote gene silencing in the fed neonates.

Discussion

The present inventors have demonstrated that dsRNA can be delivered to arthropods. Direct feeding of naked, unpackaged, dsRNA failed to produce an RNAi phenotype in D. melanogaster or H. armigera, indicating that the transfection promoting agents were necessary for effective transfection in these species. However, it is envisaged that in arthropods with a simple digestive system naked dsRNA may be affective in obtaining gene silencing.

Notably, the same transfection promoting agents were effective at delivering dsRNA in D. melanogster and H. armigera, despite the pH differences in the guts of these two species.

A significant finding was that dsRNA that had been previously processed within one arthropod could still facilitate RNAi in another arthropod, even when the RNA was purified from its associated proteins. It is anticipated that the purification process would remove all dsRNA-associated proteins, such as the so-called dicer proteins, which are believed to mediate target RNA degradation. Assuming that the majority of the dsRNA purified from the arthropods, and subsequently ingested by the neonates was the processed 21- and 22-mer oligonucleotides, it appears that the effective functional unit in the latter experiment is the short oligonucleotides. However, longer lengths of dsRNA are clearly effective once ingested, as evidenced by the ingestion of in vitro transcribed GUS and vATPase dsRNAs.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All publications discussed above are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed, particularly in Australia, before the priority date of each claim of this application.

REFERENCES

Allen, T. M. and Chonn, A. (1987) FEBS Lett. 223:42-46.
Bosher, J. M., and Labouesse, M. (2000) Nature Cell Biol 2: E31-E36.
Bradford, M. M. (1976) Anal. Biochem. 72: 248-54.
Cameron, F. H., Moghaddam, M. J., Bender, V. J., Whittaker, R. G., Mott, M., Lockett, T. J. (1999) Biochim. Biophys. Acta/Biomembranes. 1417: 37-50.
Dougherty, W. G. and Parks, T. D. (1995) Curr. Opin. Cell Biol. 7:399-405.
Duve, H., Johnsen, A. H., Maestro, J. L., Scott, A. G., Winstanley, D., Davey, M., East, P. D, Thorpe, A. (1997) Peptides 18: 1301-1309.
Elbashir, S. M., Harborth, J., Lendeckel, W., Yalcin, A., Weber, K., and Tuschl, T. (2001) Nature 411: 494-498.
Gallagher, S. 1992 Quantitation of GUS activity by fluorometry. In: GUS Protocols (ed S. Gallagher). Academic Press Inc. San Diego.
Gawron-Burke, C. and Baum, J. A. 1991. Genetic manipulation of Bacillus thuringiensis insecticidal crystal protein genes in bacteria p. 237-263 In J. K. Setlow (ed.) Genetic engineering: principles and methods, vol 13 Plenum Press, New York.).

Maeda I., Kohara, Y., Yamamoto, M., and Sugimoto, A. (2001) Current Biology 11: 171-176.

Naleway, J. 1992 Histochemical, spectrophotometric, and fluorometric GUS substrates. In: GUS Protocols (ed S. Gallagher). Academic Press Inc. San Diego.

Needleman, S. B. and Wunsch, C. D. (1970) J. Mol. Biol. 48:443-453.

Pinkerton, A. C., O'Brochta, D., and Atkinson, P W. (1996) Insect Molec. Biol. 5: 223-227.

Roberts, D. B. and Standen, G. N. (1998) The elements of *Drosophila* biology and genetics. In: *Drosophila*: A Practical Approach (ed. D. B. Roberts) Oxford University Press, Oxford.

Sambrook, J., Fritsch, E. F., and Maniatis, T. (1989) Molecular Cloning: a Laboratory Manual. Cold Springs Harbor Laboratory, New York.

Spradling, A. C., and Rubin, G. M. (1982) Science 218: 341-347.

Tabara, H., Grishok, A., and Mello, C. C. (1998) Science 282: 430-431.

Thummel, C. S., Boulet, A. M., Lipshitz, H. D. 1988. Gene 74: 445-456

Timmons, L. and Fire, A. (1998) Nature 395: 854.

Waterhouse, P. M., Graham, M. W., and Wang, M.-B. (1998) Proc. Natl. Acad. Sci. 95:13959-13964.

Waterhouse, P. M., Wang, M.-B., Lough, T. (2001) Nature 411: 834-842.

White, 1988. The anatomy. In: The nematode *Caenorhabditis* (W. B. Wood ed.) Cold Spring Harbor Press, NY Wu, N. Z., Da, D., Rudoll, T. L., Needham, D., Whorton, A. R. and Dewhirst, M. W. (1993) Cancer Res. 53:3765-3770.

The invention claimed is:

1. A method of reducing the level of a target RNA in a lepidopteran or dipteran insect comprising feeding to the insect in a larval stage a composition comprising a dsRNA molecule and phosphatidylcholine, wherein the dsRNA molecule specifically reduces the level of the target RNA in a cell of the insect.

2. The method of claim 1, wherein production of a protein encoded by the target RNA is reduced.

3. The method of claim 1, wherein the method comprises wholly or partially soaking the insect in the composition comprising the dsRNA.

4. The method of claim 3, wherein the composition further comprises a nucleic acid condensing agent.

5. The method of claim 4, wherein the nucleic acid condensing agent is selected from the group consisting of: spermidine and protamine sulfate.

6. The method of claim 1, wherein the dsRNA is from a transgenic organism expressing the dsRNA.

7. The method of claim 6, wherein the transgenic organism is a transgenic plant.

8. The method of claim 1, wherein the dsRNA comprises a nucleotide sequence having at least 90% identity to at least a portion of the sequence of the target RNA.

9. The method of claim 1, wherein the dsRNA molecule comprises 21 contiguous nucleotides in a sequence identical to the sequence of a portion of the target RNA.

10. The method of claim 1, wherein the dsRNA confers lethality on the lepidopteran or dipteran insect.

11. The method of claim 9, wherein the portion of the dsRNA which is double stranded is 21 to 50 base pairs in length.

12. The method of claim 1, wherein the dsRNA is partially double-stranded.

13. The method of claim 1, wherein the dsRNA is formed by a single self-complementary RNA strand.

14. The method of claim 13, wherein the self-complementary RNA strand has a region of self-complementarity of which the sense sequence consists of 20 to 23 contiguous nucleotides identical in sequence to 20 to 23 contiguous nucleotides of the target RNA.

15. The method of claim 1, wherein the dsRNA is formed by two complementary RNA strands.

16. The method of claim 15, wherein the portion of the dsRNA which is double stranded is 21 to 23 basepairs in length.

17. The method of claim 16, wherein the dsRNA is fully double-stranded.

18. The method of claim 1, wherein the effect on the lepidopteran or dipteran insect is death or sterility.

19. A method of reducing the level of an RNA in a lepidopteran or dipteran insect comprising delivering to a lepidopteran or dipteran insect larva a composition comprising a dsRNA molecule and phosphatidylcholine, wherein the composition is ingested by the larva, and wherein the dsRNA molecule comprises 21 contiguous nucleotides in a sequence identical to the sequence of a portion of the RNA in the larva.

20. The method of claim 19, wherein the portion of the dsRNA which is double stranded is 21 to 23 basepairs in length.

* * * * *